United States Patent
Wu et al.

(10) Patent No.: US 10,524,950 B2
(45) Date of Patent: Jan. 7, 2020

(54) MODULAR SEMI-ACTIVE JOINT EXOSKELETON

(71) Applicant: The Regents of the University of California, Oakland, CA (US)

(72) Inventors: Shang-Li Wu, Albany, CA (US); Homayoon Kazerooni, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/898,102

(22) Filed: Feb. 15, 2018

(65) Prior Publication Data

US 2018/0243120 A1    Aug. 30, 2018

Related U.S. Application Data

(60) Provisional application No. 62/459,564, filed on Feb. 15, 2017.

(51) Int. Cl.
*A61F 2/64* (2006.01)
*A61F 5/01* (2006.01)
(Continued)

(52) U.S. Cl.
CPC ............ *A61F 5/0125* (2013.01); *A61F 2/644* (2013.01); *A61F 2/68* (2013.01); *A61F 5/0123* (2013.01);
(Continued)

(58) Field of Classification Search
CPC .......... A61F 2/642; A61F 2/644; A61F 2/646; A61F 2005/0141; A61F 2005/0144
(Continued)

(56) References Cited

U.S. PATENT DOCUMENTS

| 3,823,424 A | * | 7/1974 | May | A61F 2/644 |
| | | | | 623/39 |
| 4,310,932 A | * | 1/1982 | Nader | A61F 2/644 |
| | | | | 623/39 |

(Continued)

FOREIGN PATENT DOCUMENTS

| GB | 2181352 | 4/1987 | |
| WO | WO2004000178 A1 * | 12/2003 | ............ A61F 2/644 |
| WO | 2018152363 A1 | 8/2018 | |

OTHER PUBLICATIONS

"Int'l Application Serial No. PCT/US18/18421, Int'l Search Report and Written Opinion dated Jun. 7, 2018", 10 pages.

*Primary Examiner* — David H Willse
(74) *Attorney, Agent, or Firm* — Kwan & Olynick LLP

(57) ABSTRACT

Systems, methods, and apparatus provide an artificial knee. Such artificial knees may include a thigh link configured to move in unison with a thigh of the person, a shank link configured to be rotatably coupled to the thigh link, and a compression spring rotatably coupled to the thigh link at a first end and coupled to the shank link at a second end. The compression spring is configured to provide an extension torque between the thigh link and the shank link during a first range of motion of the thigh link and the shank link relative to each other. The compression spring is configured to provide a flexion torque between the thigh link and the shank link during a second range of motion of the thigh link and the shank link relative to each other.

11 Claims, 29 Drawing Sheets

(51) Int. Cl.
*A61F 2/68* (2006.01)
*B25J 9/00* (2006.01)
*A61F 2/50* (2006.01)

(52) U.S. Cl.
CPC ....... *B25J 9/0006* (2013.01); *A61F 2002/503* (2013.01); *A61F 2002/5018* (2013.01); *A61F 2002/5033* (2013.01); *A61F 2002/5075* (2013.01); *A61F 2002/5079* (2013.01); *A61F 2005/0141* (2013.01); *A61F 2005/0144* (2013.01); *A61F 2005/0158* (2013.01); *A61F 2005/0169* (2013.01); *A61F 2005/0179* (2013.01)

(58) Field of Classification Search
USPC .............................................. 623/43, 44, 46
See application file for complete search history.

(56) References Cited

U.S. PATENT DOCUMENTS

| | | | |
|---|---|---|---|
| 5,376,137 A | | 12/1994 | Shorter et al. |
| 6,086,616 A | * | 7/2000 | Okuda ................... A61F 2/644 |
| | | | 623/44 |
| 2003/0093018 A1 | | 5/2003 | Albrecht et al. |
| 2016/0324665 A1 | | 11/2016 | Boiten |
| 2016/0374887 A1 | | 12/2016 | Wu et al. |

* cited by examiner

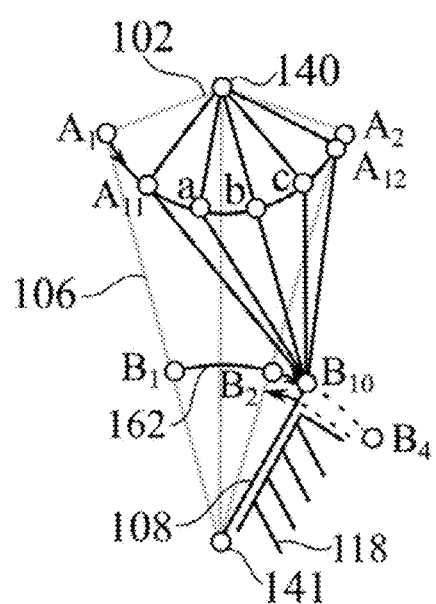 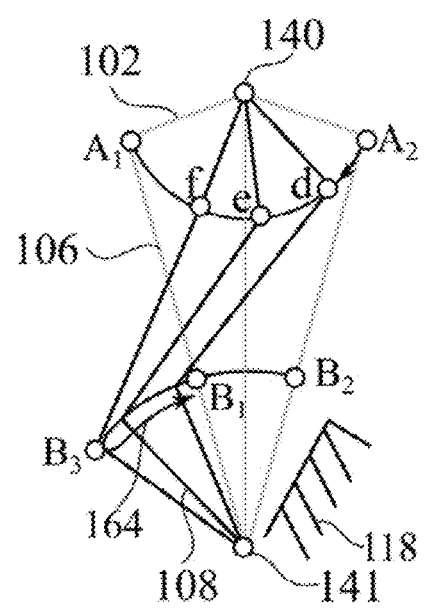
*FIG. 5A*  *FIG. 5B*

$\theta_{KNEE} = \theta_{START}$ $\theta_{KNEE} = \theta_{ENG}$ $\theta_{KNEE} = \theta_{TOE}$ $\theta_{KNEE} = \theta_{REL}$ $\theta_{KNEE} = \theta_{END}$

MODULAR SEMI-ACTIVE JOINT EXOSKELETON

CROSS-REFERENCE TO RELATED APPLICATIONS

This application claims the benefit under 35 U.S.C. § 119(e) of U.S. Provisional Patent Application No. 62/459,564, filed on 2017 Feb. 15, which is incorporated herein by reference in its entirety for all purposes.

STATEMENT OF GOVERNMENT SUPPORT

This invention was made with government support under Contract No. 1545106 awarded by the National Science Foundation. The government has certain rights in this invention.

TECHNICAL FIELD

The present disclosure pertains to artificial lower limb prosthetics and orthotic systems and more particularly, to an exoskeleton knee that can be used for a variety of orthotic applications.

BACKGROUND

A traditional knee-ankle-foot orthosis (KAFO) is used to increase the patient stability during the weight-bearing phase of walking. A traditional KAFO locks the knee in full extension, which provides stability. This locked posture results in patients' ability to ambulate with gait deviations that can lead to overuse injuries. A stance control orthosis (SCO) allows the knee to flex during the swing phase of the gait cycle and prevents knee flexion for stability during the stance phase. By allowing the knee to bend during the swing phase, SCOs allow a more natural gait, which may reduce secondary complications from gait compensations and allow the patient to walk with less effort.

FILLAUER® developed a gravity-actuated knee joint locking system for its Swing Phase Lock (SPL) orthosis (U.S. Patent 2003/0153854). A Swing Phase Lock uses a simple internal pendulum mechanism mounted on the thigh link (the member that moves in unison with the user's thigh). As the thigh link moves, the pendulum swinging motion locks and unlocks the shank link (the member that moves in unison with the user's shank) relative to the thigh link. This allows for locking and unlocking of the knee joint for appropriate phases of a walking cycle.

Free Walk orthosis (marketed by OTTOBOCK®) and UTX orthosis (marketed by BECKER®) work based on the principle. The dorsiflexion of the foot at the end of the stance pulls on controllable cable connected to a locking mechanism at the knee joint. This pulling action disengages the locking mechanism for swing. The locking mechanism is spring loaded and locks the knee when the knee is fully extended.

Sensor Walk (manufactured by OTTOBOCK®) uses a wrap spring at the knee joint for locking and unlocking the knee. This orthosis includes two sets of sensors—one at the knee to measure the knee angle and another at the footplate to measure force between the foot and the floor; a wrap spring clutch replacing the lateral knee joint to provide braking capability to support the anatomic knee joint; a microprocessor-controlled release for the brake; electronic circuitry; and a battery pack carried in a waist pack. Sensors in the footplate disengage the wrap spring clutch and allow the knee to bend in the late stance phase, when weight has been transferred to the contralateral side and is ready for single-limb support. A knee sensor senses extension of the knee after toe off and sends a signal to the microprocessor putting the wrap spring clutch in its locked position.

Horton Stance Control Orthosis (U.S. Pat. No. 6,635,024) includes a locking mechanism that locks and unlocks the knee with the help of a push rod. The push rod is placed between the heel and the knee. The push rod locks the knee at heel strike and unlocks the knee right at the end of stance phase. The device locks knee at any angle.

BRIEF DESCRIPTION OF THE DRAWINGS

FIG. 5A and FIG. 5B depict how artificial knee 100 provides support from a first singular point to a second singular point, and does not provide support from the second singular point to the first singular point.

DETAILED DESCRIPTION

Figure 1:
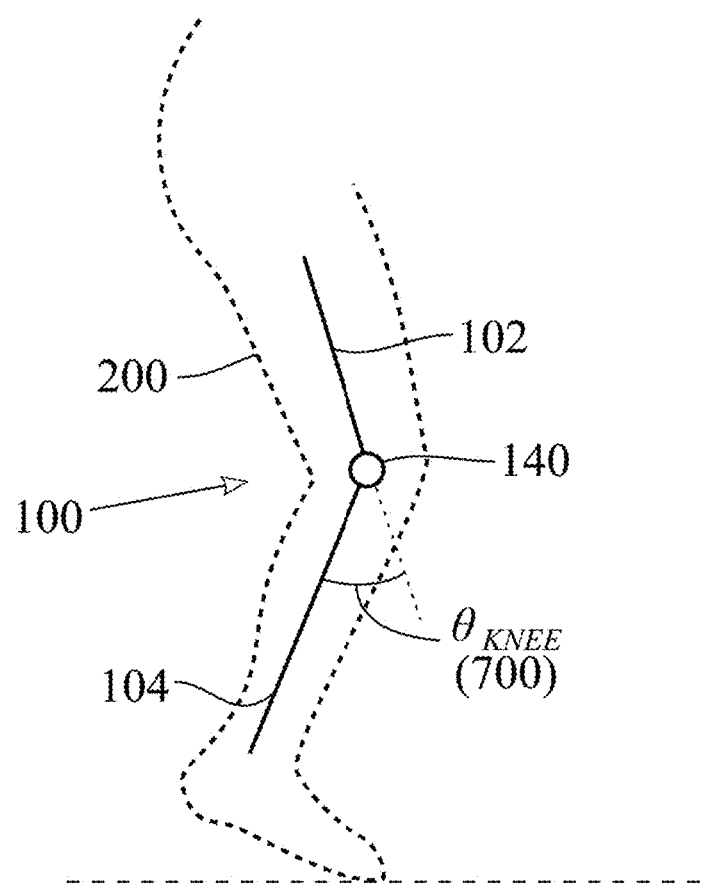
FIG. 1 depicts an embodiment of artificial knee 100 associated with person 200.

FIG. 1 shows the schematic of leg 200 of a person. Knee angle $\theta_{KNEE}$ 700 is defined as an angle between the extension of human thigh relative to the human shank as shown in FIG. 1. In various embodiments, the human knee extends if knee angle $\theta_{KNEE}$ 700 gets smaller. The human knee flexes if knee angle $\theta_{KNEE}$ 700 gets larger. Accordingly, "knee extension" or "extending the knee" refer to the situations where the human leg intends to straighten. Similarly, "knee flexion" or "flexing the knee" refer to the situations where the human leg intends to bend.

Figure 2:
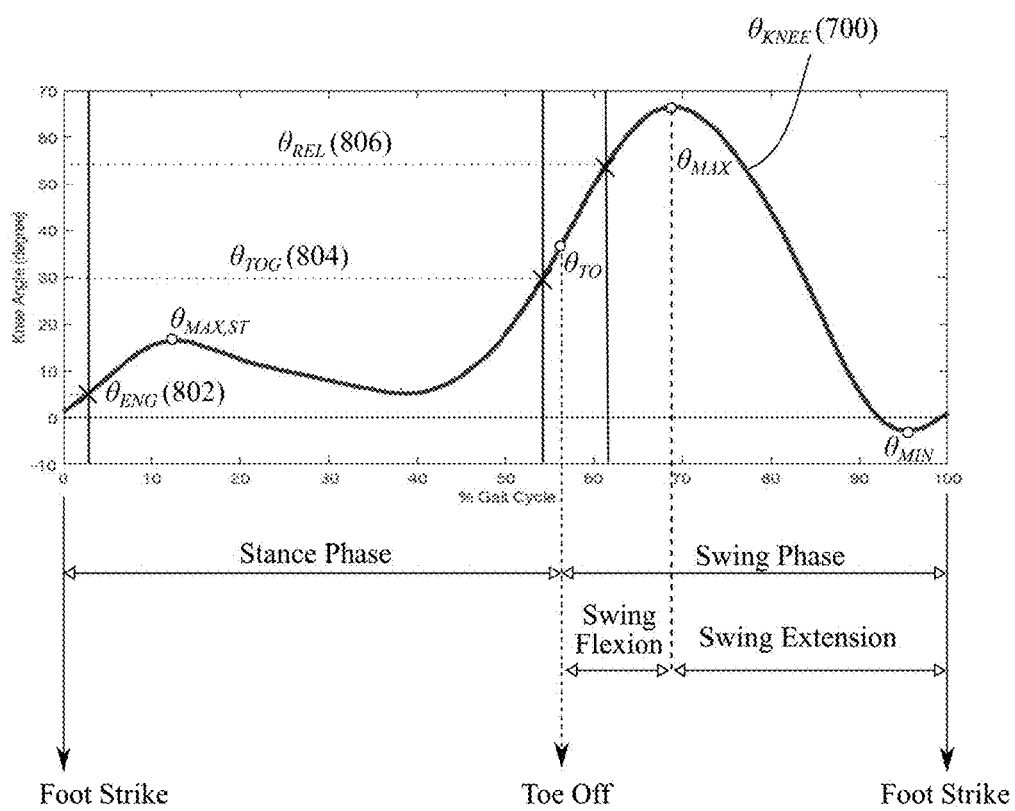
FIG. 2 depicts knee angle $\theta_{KNEE}$ 700 during a walking cycle.

FIG. 2 shows the plot of human knee angle, $\theta_{KNEE}$ 700, during a walking cycle. As seen in FIG. 2 there are two main phases in a gait cycle, a stance phase and a swing phase. The stance phase refers to the configurations when the foot is on the ground, and the swing phase refers to the configurations when the foot is off the ground. The swing phase can be subdivided into two phases: swing flexion—when the knee flexes, and swing extension—when the knee extends. In summary the gait cycle starts at foot strike. Later, the human leg enters the swing phase at toe off. The swing phase starts with a swing flexion phase, followed by the swing extension phase. As can be seen in FIG. 2, human knee angle, $\theta_{KNEE}$ 700, during the entire walking cycle, flexes to local minimums twice: once during the stance phase and once during the swing phase. During the stance phase the knee angle increases (flexes) to $\theta_{MAX,ST}$. During the swing phase, the knee reaches maximum knee flexion $\theta_{MAX}$. $\theta_{TO}$ represents the knee angle at the toe off. The knee reaches the minimum knee angle $\theta_{MIN}$ toward the end of swing phase. Although there may be variation from the plot shown in FIG. 2, generally the human knee goes through two flexions in a walking cycle: a small flexion during the stance phase and a large one during the swing phase. The small flexion is in response to the person's weight while the larger flexion provides toe clearance during the swing phase.

Artificial knee 100 (which may be either a prosthetic knee or an orthotic knee) is configured to exhibit the basic behavior of the human knee with no actuators, sensors and computers. Such a knee can be used as a low cost artificial knee 100 for various orthotic, prosthetic and exoskeleton applications. As shown in FIG. 1, artificial knee 100 comprises a thigh link 102, shank link 104, rotatably coupled to each other at knee joint 140. Based on the observation described above in FIG. 1 and FIG. 2, the artificial knee 100 is configured to exhibit three behaviors: (1) artificial knee 100 is configured to resist the knee flexion during the stance phase (this means artificial knee 100 helps the human during the stance phase to support a portion of user's weight); (2) artificial knee 100 is configured to encourage knee flexion during the swing phase to assist in toe clearance during the swing flexion phase; and (3) artificial knee 100 is configured to allow free swing extension in the swing extension phase.

The above three features facilitate the artificial knee 100 to support the user during the stance phase, but remain free during the swing extension. It further encourages the knee flexion right at early swing phase. In various embodiments, all of the above features are achieved passively without the use of actuators, computers and sensors.

Accordingly, artificial knee 100 is configured to produce an extension torque from engagement angle 802 (represented by $\theta_{ENG}$ in FIG. 2) to toggle angle 804 (represented by $\theta_{TOG}$ in FIG. 2). This means artificial knee 100 resists flexion and assists the user during the stance phase to support at least a portion of the user's weight. Extension torque is defined as a torque that causes artificial knee 100 to extend. Artificial knee 100 is further configured to provide flexion torque from toggle angle $\theta_{TOG}$ 804 to release angle 806 (represented by $\theta_{REL}$ in FIG. 2). This means artificial knee 100 encourages knee flexion during the swing phase to assist in toe clearance. Flexion torque is defined as a torque that causes artificial knee 100 to flex. In FIG. 1, flexion torque is a torque that causes $\theta_{KNEE}$ to increase. $\theta_{TOG}$ represents a knee angle that torque in the artificial knee 100 switches (toggles) from an extension torque to a flexion torque. The extension torque is needed to support the weight, while the flexion torque is needed to clear the ground. Once the knee has accomplished the above two features, it then needs to freely extend and get ready for foot strike as shown in FIG. 2. This means the mechanism that created extension torque between $\theta_{ENG}$ and $\theta_{TOG}$, and flexion torque between $\theta_{TOG}$ and $\theta_{REL}$ is configured to become ineffective when the knee is extending before foot strike. Accordingly, artificial knee 100 is configured to first provide extension torque from engagement angle $\theta_{ENG}$ 802 to toggle angle $\theta_{TOG}$ 804 and then provide flexion torque from toggle angle $\theta_{TOG}$ 804 to release angle $\theta_{REL}$ 806. In some embodiments, artificial knee 100 does not need to provide any other torque in any other phases of the knee trajectory. The state when artificial knee 100 provides extension torque is called the "extension support state". Similarly, the state when artificial knee 100 provides flexion torque is called "flexion support state".

To design artificial knee 100, one must specify angles $\theta_{ENG}$, $\theta_{TOG}$, $\theta_{REL}$ (represented by 802, 804, and 806). $\theta_{ENG}$, $\theta_{TOG}$, $\theta_{REL}$ angles correspondingly represent when the extension torque should begin, when the extension torque should switch to flexion torque, and when the flexion torque should end. The range limits of angles 802, 804, and 806 are defined by three inequalities: (1) $\theta_{MIN} < \theta_{ENG} < \theta_{MAX,ST}$; (2) $\theta_{MAX,ST} < \theta_{TOG} < \theta_{TO}$; and (3) $\theta_{TO} < \theta_{REL} < \theta_{MAX}$.

As shown in FIG. 2, $\theta_{MIN}$ is the minimum knee angle during the gait, $\theta_{MAX,ST}$ is the maximum knee angle in the stance phase, $\theta_{TO}$ is knee angle at toe off, and $\theta_{MAX}$ is the maximum knee angle throughout the gait.

If $\theta_{ENG} > \theta_{MAX,ST}$, artificial knee 100 provides no resistance during some portion of stance phase. If $\theta_{REL} < \theta_{TO}$, toe clearance will not be encouraged. In various embodiments, $\theta_{TOG}$ 804 is configured to be the same as the knee angle at toe off so flexion torque is generated as soon as toe off takes place. To prevent any extension torque after toe off (because it might hinder knee flexion), $\theta_{TOG}$ 804 is configured to be smaller than the average knee angle at toe off. Extension torque after toe off will prevent knee flexion needed for ground clearance. In various embodiments, the average minimum knee angle at toe off is approximately 35 degrees. Therefore, in one embodiment, $\theta_{TOG}$ 804 is configured to be 30 degrees. Such a configuration of $\theta_{TOG}$ 804 guarantees that toggle point of artificial knee 100 takes place before the toe off. It will be appreciated that other values for $\theta_{TOG}$ 804 may be implemented depending on the applications and other specific issues related to the user. In some embodiments, $\theta_{ENG}$ 802 is configured to be as small as possible and $\theta_{REL}$ 806 is configured to be as large as possible to create more supportive torque. However ($\theta_{REL}-\theta_{ENG}$) is within the range of normal knee operation range. This means ($\theta_{REL}-\theta_{ENG}$)< ($\theta_{MAX}-\theta_{MIN}$).

In some embodiments, $\theta_{MIN}$, $\theta_{MAX,ST}$ and $\theta_{MAX}$ are around 0, 20 and 65 degrees, respectively. Considering various gaits for different individuals, in some embodiments, artificial knee 100 may be configured such that $\theta_{ENG}$ 802 and $\theta_{REL}$ 806 are 5 and 55 degrees, respectively. It will be appreciated that other values for $\theta_{ENG}$ 802 and $\theta_{REL}$ 806 may be implemented depending on the applications and other specific issues related to the user.

Figure 3:
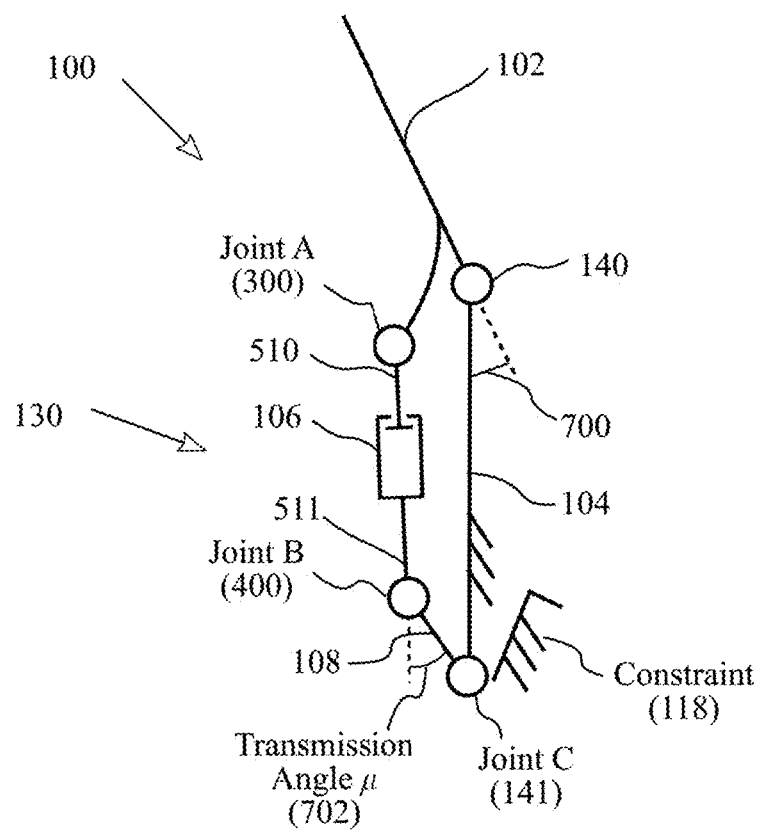
FIG. 3 depicts an embodiment of artificial knee 100.
Figure 26:
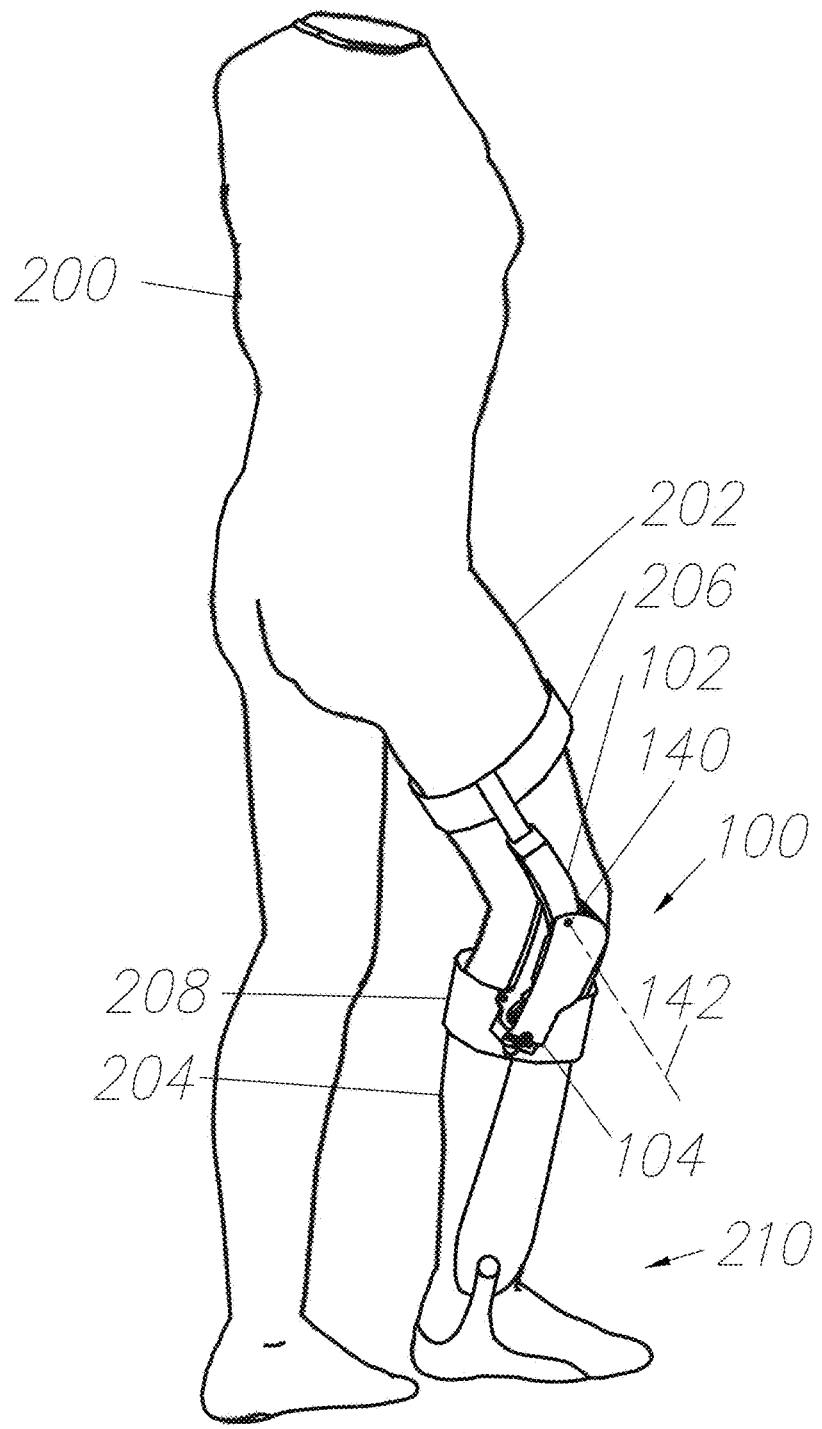
FIG. 26 shows an embodiment of artificial knee 100 worn by person 200 as an orthotics knee, and additionally shows artificial knee 100 coupled to ankle-foot orthotics 210.
Figure 27:
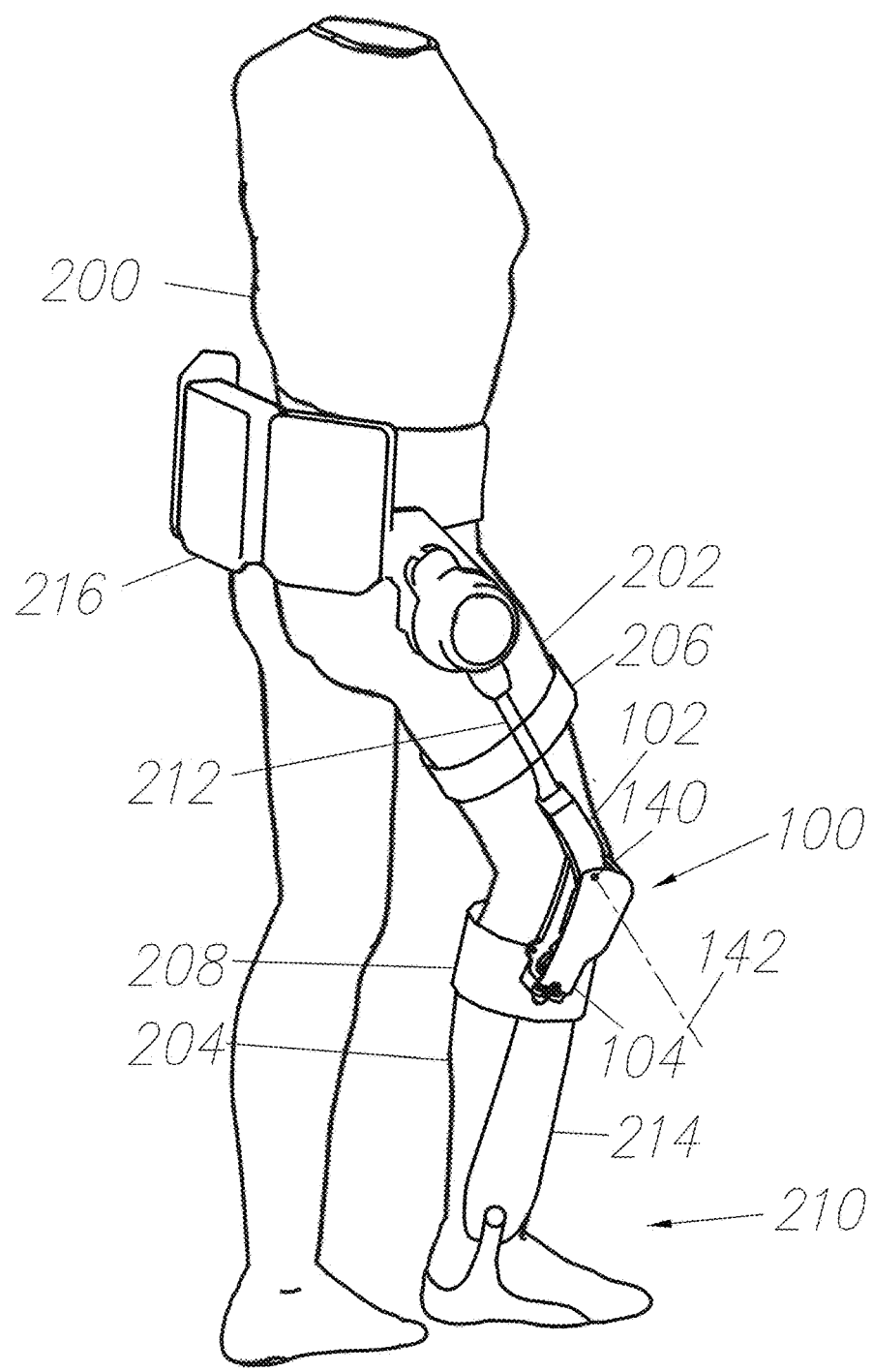
FIG. 27 shows an embodiment of artificial knee 100 worn by person 200 as an exoskeleton knee.

FIG. 3 shows the schematic of an embodiment of artificial knee 100. Artificial knee 100 comprises thigh link 102, and shank link 104 rotating about knee joint 140. Knee angle $\theta_{KNEE}$ 700 represents the angle between shank link 104 and the extension of thigh link 102. Since in orthotic and prosthetic applications, the human knee angle and the artificial knee angle coincide on each other, $\theta_{KNEE}$ 700 is used to represent both the angle of human knee and the angle of artificial knee 100. In some embodiments, such as exoskeletons or orthotic systems, thigh link 102 and shank link 104 are designed to move in unison with the human's thigh and shank. Thigh brace 206 as shown in FIG. 26 and FIG. 27 is used to couple thigh link 102 to person's thigh. In some embodiments, as shown in FIG. 26 and FIG. 27, shank brace 208 is used to couple shank link 104 to person's shank.

FIG. 3 shows that artificial knee 100 further comprises compression spring 106 rotatably coupled to thigh link 102 from its first end 510. Artificial knee 100 further comprises fourth link 108 rotatably coupled with the second end 511 of compression spring 106. Compression spring 106, fourth link 108 in addition to shank link 104 and thigh link 102 form four bar linkage 130 as shown in FIG. 3. Below describes how this four bar linkage achieves the above features mentioned above. In some embodiments, thigh link 102 and shank link 104 may be considered as a driver link and ground link of the four bar linkage 130 respectively. Further, compression spring 106 and fourth link 108 may be considered the coupler link and the follower link of four bar linkage 130. Transmission angle μ 702 is defined as the angle between fourth link 108 and compression spring 106 as shown in FIG. 3. When compression spring 106 is not compressed and it acts like a rigid link, this mechanism is a rocker-rocker four-bar linkage, which means that both driver link (thigh link 102) and follower link (fourth link 108) have reciprocating motion. Constraint 118 is fixed on shank link 104 to stop the rotation of fourth link 108 (follower link) at a certain angle. Constraint 118 can be a hard stop formed on shank link 104. In some embodiments, constraint 118 is assumed to be parallel with fourth link 108 when it blocks fourth link 108.

Figure 4A:
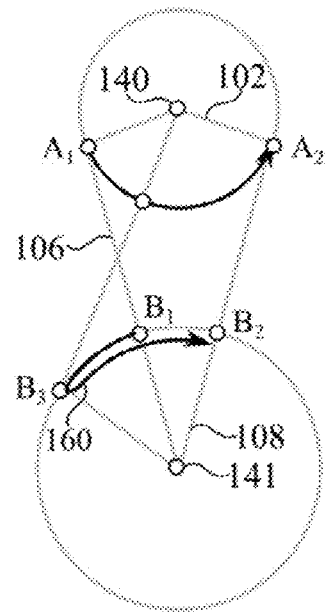
FIG. 4A, FIG. 4B, FIG. 4C, and FIG. 4D depict when thigh link 102 moves from one singular point to another.
Figure 4B:
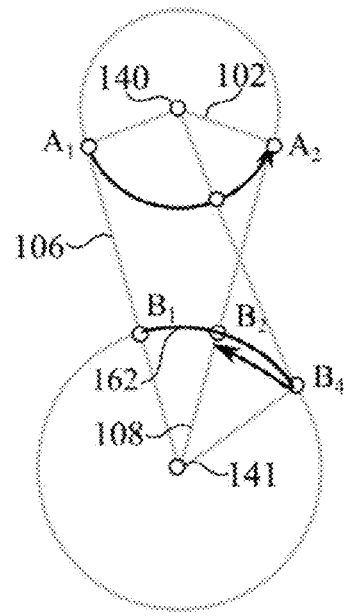
Figure 4C:
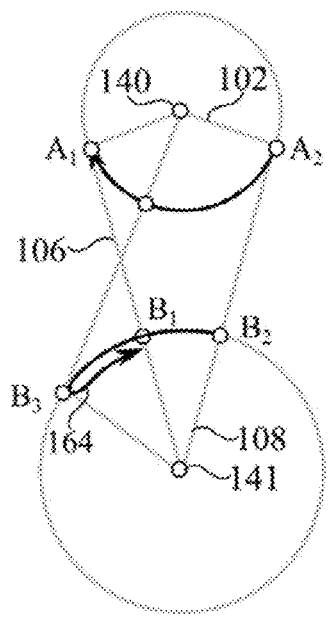
Figure 4D:
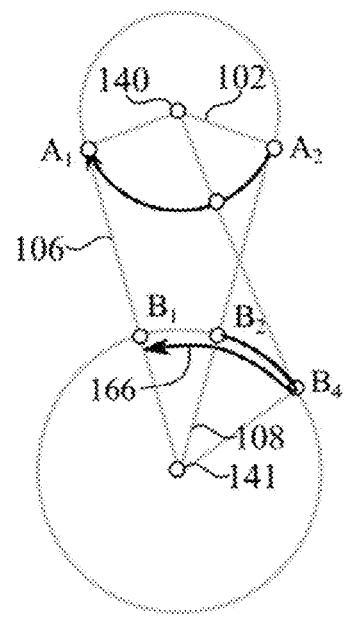

The range of motion of the thigh link 102 (driver link of four bar linkage 130) is defined by the singular points where compression spring 106 (coupler link for four bar linkage 130) aligns with fourth link 108 (i.e., transmission angle μ 702 is 0). FIG. 4A through FIG. 4D show several properties of four bar linkage 130. FIG. 4A shows artificial knee 100 when thigh link 102 moves from one singular configuration $A_1$ to another singular configuration $A_2$. At each singular configuration, fourth link 108 has two options to move: it can either follow trajectory 160 in FIG. 4A or follow trajectory 162 shown in FIG. 4B. Singular configurations are the only points that fourth link 108 has these two options. FIG. 4A and FIG. 4B show configurations where thigh link 102 moves from $A_1$ counter-clockwise to $A_2$. Fourth link 108 is initially located at singular point $B_1$. If fourth link 108 is perturbed to start moving counter-clockwise as shown in FIG. 4A, then trajectory 160 shows how fourth link 108 moves from $B_1$ to $B_2$. FIG. 4B shows the same mechanism where thigh link 102 moves from $A_1$ to $A_2$, however fourth link 108 is initially perturbed to a clockwise direction where it moves from $B_1$ to $B_2$ along trajectory 162. FIG. 4C and FIG. 4D show configurations where thigh link 102 moves clockwise from $A_2$ to $A_1$. Fourth link 108 is initially located at singular point $B_2$. If fourth link 108 is perturbed to start moving counter-clockwise as shown in FIG. 4C, then trajectory 164 shows how fourth link 108 moves from $B_2$ to $B_1$. FIG. 4D shows the same mechanism where thigh link 102 moves from $A_2$ to $A_1$ clockwise however fourth link 108 is initially perturbed to a clockwise direction where it moves from $B_2$ to $B_1$ along trajectory 166.

Turning to FIG. 4B and FIG. 4C, the operation of four bar linkage 130 is described when fourth link 108 (follower link) is perturbed to travel along trajectory 162 when thigh link 102 travels from $A_1$ to $A_2$, and along trajectory 164 when thigh link 102 travels back from $A_2$ to $A_1$. As shown in FIG. 4B, fourth link 108 is perturbed to move along trajectory 162 at point $B_1$. While thigh link 102 moves from $A_1$ to $A_2$ counter-clockwise, fourth link 108 (follower link) moves from $B_1$ to $B_2$ and to $B_4$, and then back to $B_2$ along trajectory 162. If fourth link 108 is perturbed to go along trajectory 164 (as shown in FIG. 4C), then fourth link 108 moves from $B_2$ to $B_1$ and to $B_3$ and then back to $B_2$ along trajectory 164, when thigh link 102 moves from $A_2$ to $A_1$ in clockwise direction. FIG. 4B and FIG. 4C show how four bar linkage 130 operates for an entire cycle of thigh link 102, if fourth link 108 is perturbed at point $B_1$ and $B_2$ along trajectories 162 and 164.

In some embodiments, constraint 118 is placed to block fourth link 108 between $B_2$ and $B_4$, as shown in FIG. 5. FIG. 5A represents artificial knee 100 when thigh link 102 rotates counter-clockwise from $A_1$ to $A_2$. FIG. 5B represents artificial knee 100 when thigh link 102 rotates clockwise from $A_2$ to $A_1$. When thigh link 102 moves from $A_1$ to $A_2$ counter-clockwise (as shown in FIG. 5A), constraint 118 blocks fourth link 108. $B_{10}$ represents joint B when fourth link 108 (follower link) becomes constrained. Similarly $A_{11}$ represents joint A when fourth link 108 (follower link) becomes constrained. Since coupler link (compression spring 106) is compressible, as thigh link 102 continues to move clockwise, coupler link (compression spring 106) gets compressed and resists the rotation of thigh link 102 relative to shank link 104. Points a, b, and c represent the locations of joint A when thigh link 102 travels from $A_{11}$ to $A_{12}$ while fourth link 108 (follower link) is not moving. When thigh link travels from $A_{12}$ to $A_2$, fourth link 108 (follower link) travels from $B_{10}$ to $B_2$. A small torque applying on the fourth link 108, when fourth link 108 is at $B_2$, pushes fourth link 108 away from constraint 118. At this time, when thigh link 102 moves back from $A_2$ clockwise (as shown in FIG. 5B), fourth link 108 moves along trajectory 164 with no constraint as shown in FIG. 5B. This means thigh link 102 moves from $A_2$ to $A_1$ through points d, e, and f with no resistance from compression spring 106. Once thigh link 102 reaches point $A_1$, another small torque pushes fourth link 108 at $B_1$ to be on trajectory 162. The behavior described above represents a situation where when thigh link 102 moves from $A_1$ to $A_2$, it will experience resistance from compression spring 106; however, from $A_2$ to $A_1$ thigh link 102 will not experience any resistance from compression spring 106.

Figure 6:
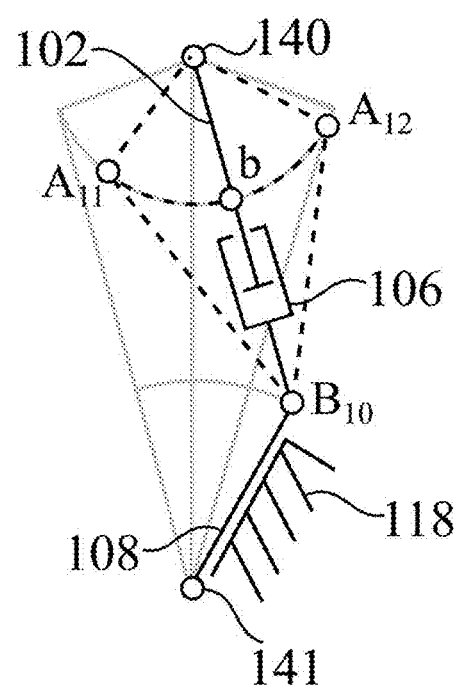
FIG. 6 depicts artificial knee 100 in a configuration as a toggle switch.

FIG. 6 shows artificial knee 100 as shown in FIG. 5A. Points $A_{11}$ and $A_{12}$ represent the locations of thigh links 102 when follower link (fourth link 108) is constrained. Both thigh link 102 and compression spring 106 (coupler link) are shown by dashed lines in these boundary locations where fourth link 108 (follower link) is constrained. As can be seen in FIG. 6, compression spring 106 starts to compress and resist the motion of thigh link 102 when thigh link 102 is at point $A_{11}$. This compression continues until joint A reaches point b where compression spring is at its shortest length. This means from $A_{11}$ to b, compression spring 106 provides extension torque for artificial knee 100. After point b, when thigh link 102 travels toward $A_{12}$, compression spring 106 switches its extension torque to flexion torque. This means the flexion motion of thigh link 102 from b to $A_{12}$ is encouraged by compression spring 106. As shown in FIG. 6, when fourth link 108 (follower link) is constrained, compression spring 106 (coupler link) provides a compression force that passes through the coupling location of thigh link 102 relative to shank link 104 (joint 140) when thigh link 102 is at point b (toggle point). At point b, thigh link 102 and compression spring 106 are aligned and compression spring 106 is at its shortest length. The toggle point, b, is an unstable equilibrium point for compression spring 106. When thigh link 102 moves from $A_{11}$ toward point b, compression spring 106 provides an extension torque between thigh link 102 and shank link 104. When thigh link 102 moves from b toward point $A_{12}$, compression spring 106 provides a flexion torque between thigh link 102 and shank link 104.

As described above, at singular points (point $B_1$ and $B_2$), small torques are applied to fourth link 108 to perturb fourth link 108 to move along trajectories 162 and 164 because driver link (thigh link 102) loses its ability to move four bar linkage 130. These torques are provided by first and second leaf springs 120 and 122 as described below.

The operation of artificial knee 100 in a gait cycle is shown in FIG. 7. FIG. 7A shows that artificial knee 100 is at a singular point where coupler link (compression spring 106) aligns with the follower link (fourth link 108). Joint A is located at point $A_1$ and joint B is located at $B_1$. Knee angle 700 at this instance is defined as start angle $\theta_{START}$ 800. With the application of a small torque along direction 600 on follower link (fourth link 108), follower link (fourth link 108) moves clockwise to break away from singular point and ultimately transition the transmission angle μ to a negative value.

As thigh link rotates counter-clockwise (artificial knee 100 flexes), follower link (fourth link 108) rotates toward constraint 118 until fourth link 108 (follower link) encounters constraint 118 as shown in FIG. 7 (B). Joint B is located at point $B_{10}$ and joint A is $A_{11}$. At this point, compression spring 106 begins to provide an extension torque as artificial knee 100 continues to flex. Knee angle $\theta_{KNEE}$ 700, at this instance is called engagement angle $\theta_{ENG}$ 802 where the "extension support state" starts.

Figure 7A:
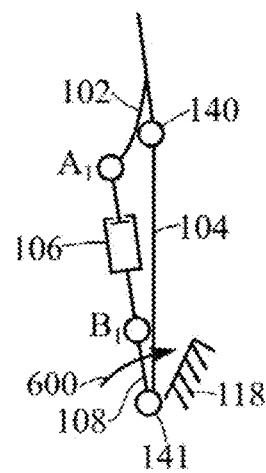
FIG. 7A, FIG. 7B, FIG. 7C, FIG. 7D, FIG. 7E, and FIG. 7F depict how artificial knee 100 operates in a gait cycle.
Figure 7B:
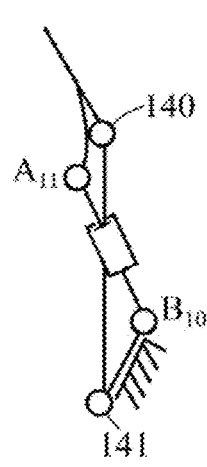
Figure 7C:
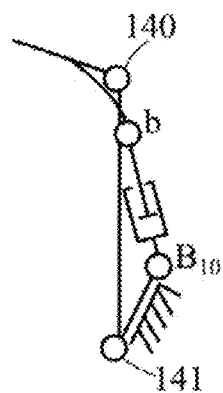

When thigh link 102 continues to rotate counter clockwise, there is a point where thigh link 102 aligns with coupler link (compression spring 106) as shown in FIG. 7C. At this point, the extension torque generated by coupler link (compression spring 106) switches its direction and becomes a flexion torque. The knee angle $\theta_{KNEE}$ 700 at this instance is called toggle angle $\theta_{TOG}$ 804 where the "flexion support state" starts. Joint A 300 is located at point b where the compression force of compression spring 106 passes through knee joint 140.

Figure 7D:
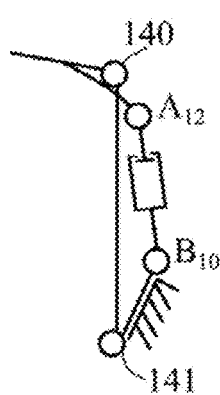

The flexion torque exists until coupler link (compression spring 106) reaches its original length as shown in FIG. 7(D). Knee angle $\theta_{KNEE}$ 700, at this point, is defined as the release angle $\theta_{REL}$ 806. Joint A is at point $A_{12}$.

Thigh link 102 continues to rotate counter-clockwise until it reaches another singular point when knee angle $\theta_{KNEE}$ 700 is at end angle $\theta_{END}$ 808 as shown in FIG. 7 (E). At this instance joint A is at point $A_2$ and joint B is at point $B_2$. At this instance, a small torque on follower link (fourth link 108), along direction 602, causes follower link (fourth link 108) to rotate away from constraint 118. Transmission angle μ at this time switches from negative to positive.

Figure 7E:
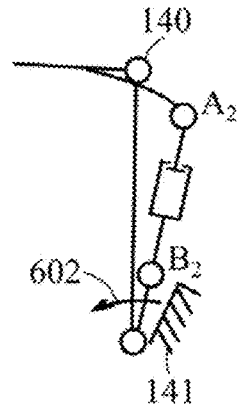
Figure 7F:
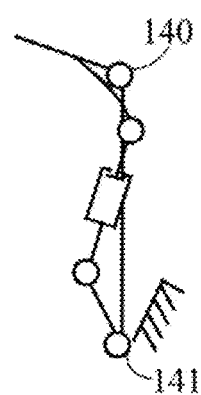

During knee extension as shown in FIG. 7F, thigh link 102 rotates clockwise, and follower link (fourth link 108) rotates away from constraint 118. No torque resists thigh link 102 clockwise motion. Thigh link 102 rotates clockwise (knee extension) and returns back to the configuration shown in FIG. 7A where artificial knee 100 is again at a singular point at which the transmission angle μ is on the verge of shifting signs.

The configuration of artificial knee 100 between FIG. 7E and FIG. 7A is considered the first free state because thigh link 102 encounters no resistance when it rotates clockwise. The configuration of artificial knee 100 between FIG. 7A and FIG. 7B is considered the second free state because thigh link 102 again encounters no resistance when it rotates counter-clockwise. The configuration of artificial knee 100 between FIG. 7B and FIG. 7C is considered the extension support state because compression spring 106 provides extension torque between thigh link 102 and shank link 104. The configuration of artificial knee 100 between FIG. 7C and FIG. 7D is considered the flexion support state because compression spring 106 provides flexion torque between thigh link 102 and shank link 104. The configuration of artificial knee 100 between FIG. 7D and FIG. 7E is considered the third free state because thigh link 102 encounters no resistance when it rotates counter clockwise.

Figure 8:
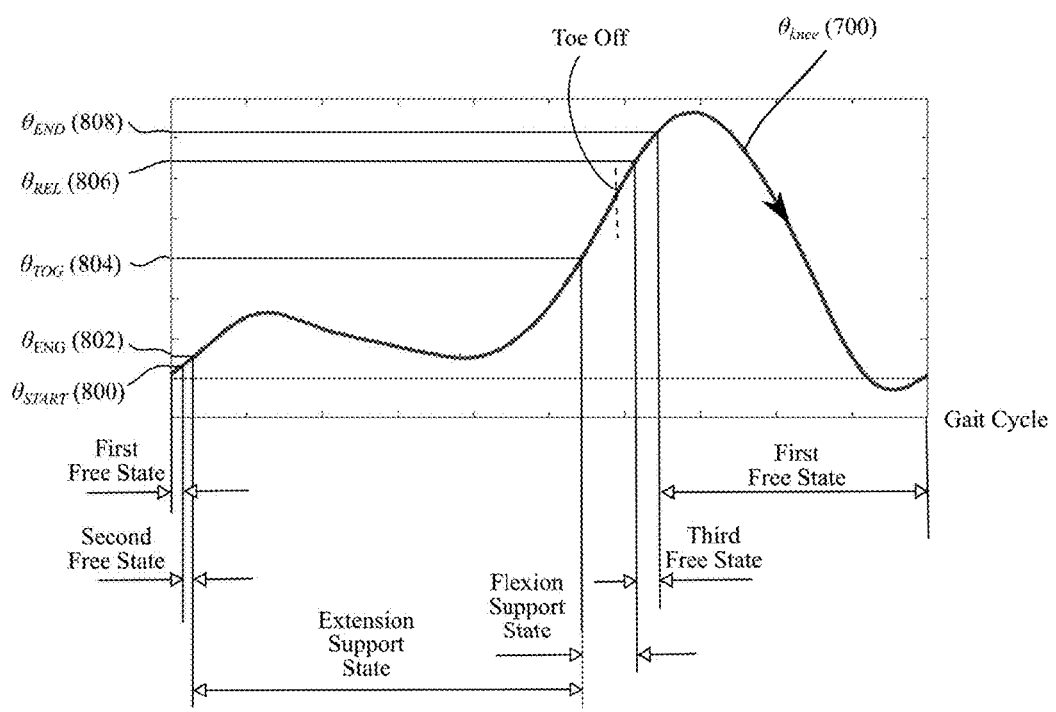
FIG. 8 depicts individual states of artificial knee 100 in a gait cycle as a function of knee angle $\theta_{KNEE}$ 700.

FIG. 8 depicts the states of artificial knee 100 defined above. Artificial knee 100 is in the first free state when it is flexing and knee angle $\theta_{KNEE}$ 700 is not larger than start angle $\theta_{START}$ 800. Artificial knee 100 is in the second free state when it is flexing and knee angle $\theta_{KNEE}$ 700 is between start angle $\theta_{START}$ 800 and engagement angle $\theta_{ENG}$ 802. Artificial knee 100 is in the extension support state when knee angle $\theta_{KNEE}$ 700 is between engagement angle $\theta_{ENG}$ 802 and toggle angle $\theta_{TOG}$ 804. Artificial knee 100 is in the flexion support state when it is flexing and knee angle $\theta_{KNEE}$ 700 is between toggle angle $\theta_{TOG}$ 804 and release angle $\theta_{REL}$ 806. Artificial knee 100 is in the third free state when knee angle $\theta_{KNEE}$ 700 is between release angle $\theta_{REL}$ 806 and end angle $\theta_{END}$ 808.

Figure 9:
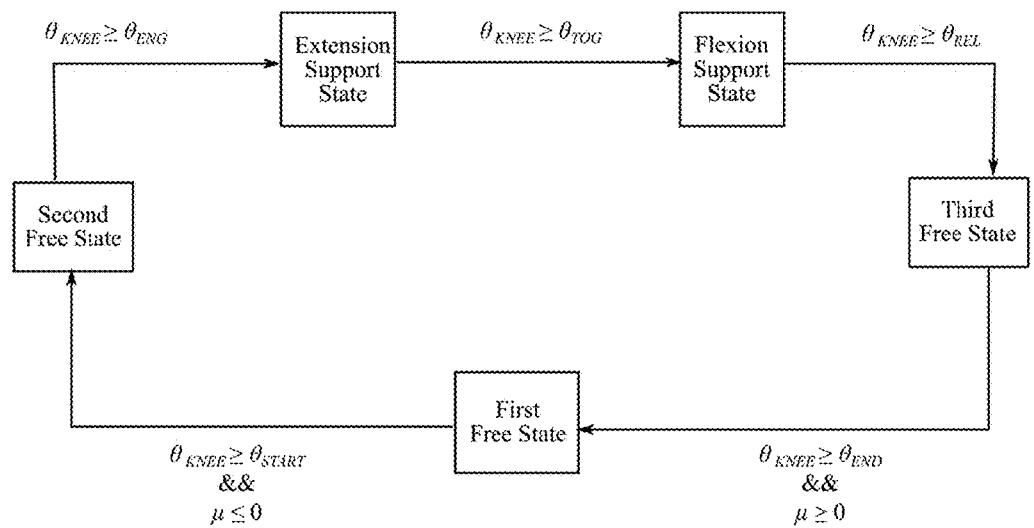
FIG. 9 depicts the finite state machine of artificial knee 100.

FIG. 9 depicts the behavior of artificial knee 100 as a finite state machine. The solid lines show when artificial knee 100 is operated normally as knee angle $\theta_{KNEE}$ 700 follows the data as shown in FIG. 8.

FIG. 10 depicts artificial knee 100, in one embodiment, having extension link 112 that allows knee angle $\theta_{KNEE}$ 700 to expand larger than the knee angle at the singular configurations, i.e., start angle $\theta_{START}$ 800 and then end angle $\theta_{END}$ 808. In one embodiment, extension link 112 can be an extension spring that is capable of lengthening the coupler but always tends to return the coupler to its shortest length. Extension link 112 acts as a rigid link when it is not pulled so the aforementioned operation is not affected, but becomes extendable when the knee reaches outside the boundary of the singular configurations.

Figure 10A:
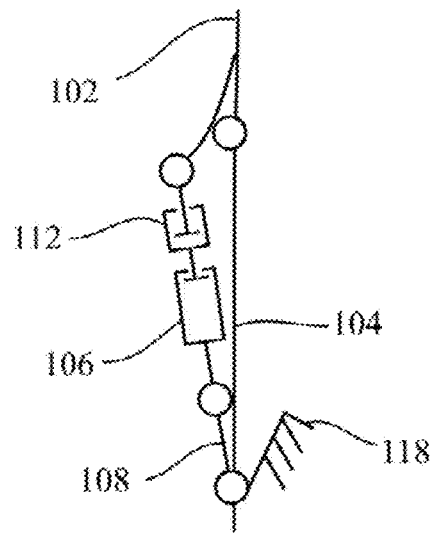
FIG. 10A, FIG. 10B, FIG. 10C, and FIG. 10D depict artificial knee 100, in one embodiment, having extension link 112 which allows knee angle $\theta_{KNEE}$ 700 to have a larger range of motion without impeding the operation in a gait cycle.
Figure 10B:
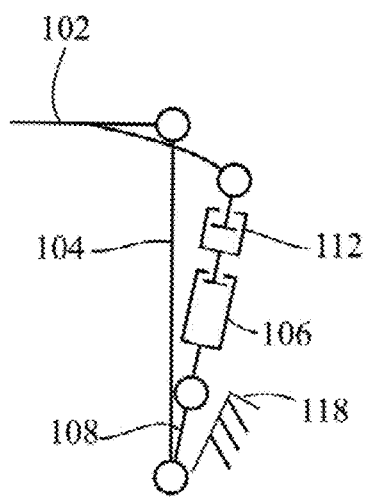

FIG. 10A and FIG. 10B show one embodiment of artificial knee 100 with extension link 112, where the first end of extension link 112 is rotatably coupled to thigh link 102, and the second end of extension link 112 is linearly coupled to the first end 510 of compression spring 106. FIG. 10A depicts artificial knee 100 with extension link 112 that allows knee angle $\theta_{KNEE}$ 700 to be about 0 degrees. FIG. 10B depicts artificial knee 100 with extension link 112 that allows the knee angle $\theta_{KNEE}$ 700 to be about 90 degrees.

Figure 10C:
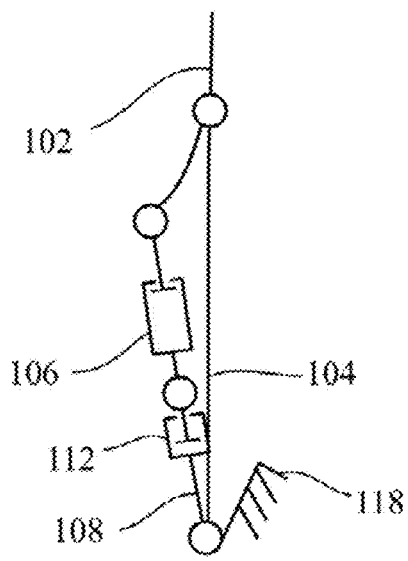
Figure 10D:
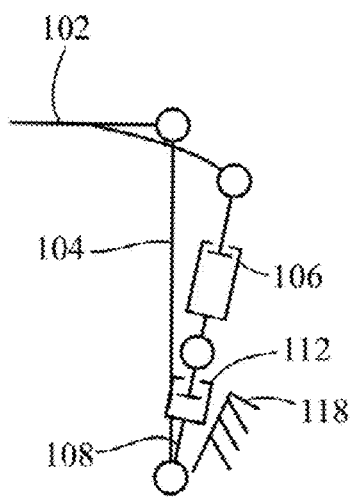

FIG. 10C and FIG. 10D show another embodiment of artificial knee 100 with extension link 112, where the first end of extension link 112 is rotatably coupled to the second end 511 of compression spring 106, and the second end of extension link 112 is linearly coupled to follower link (fourth link 108). FIG. 10C depicts artificial knee 100 with extension link 112 that allows knee angle $\theta_{KNEE}$ 700 to be about 0 degrees. FIG. 10D depicts artificial knee with extension link 112 that allows knee angle $\theta_{KNEE}$ 700 to be about 90 degrees.

Figure 11:
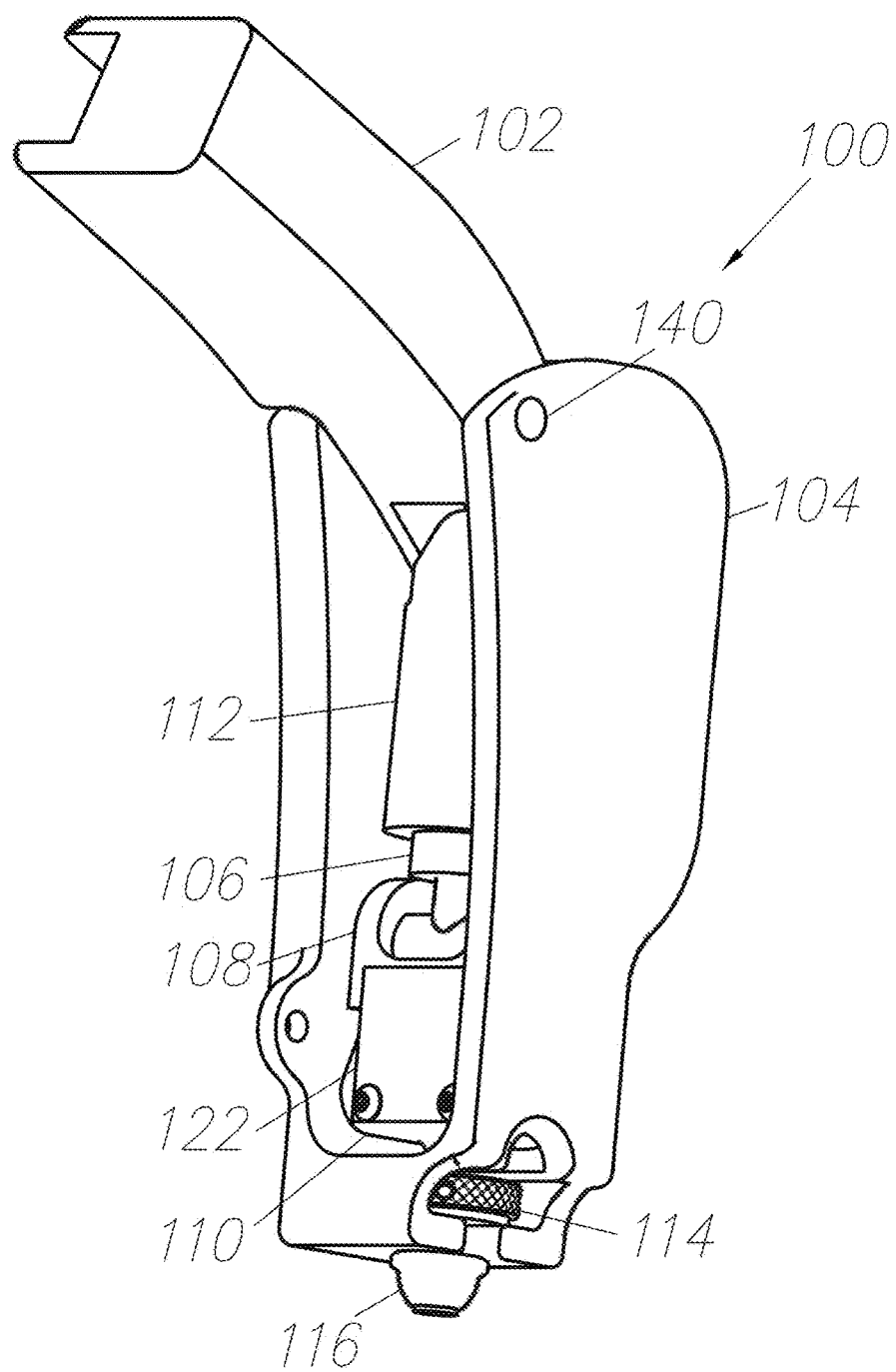
FIG. 11 depicts one embodiment of a mechanical configuration.
Figure 12:
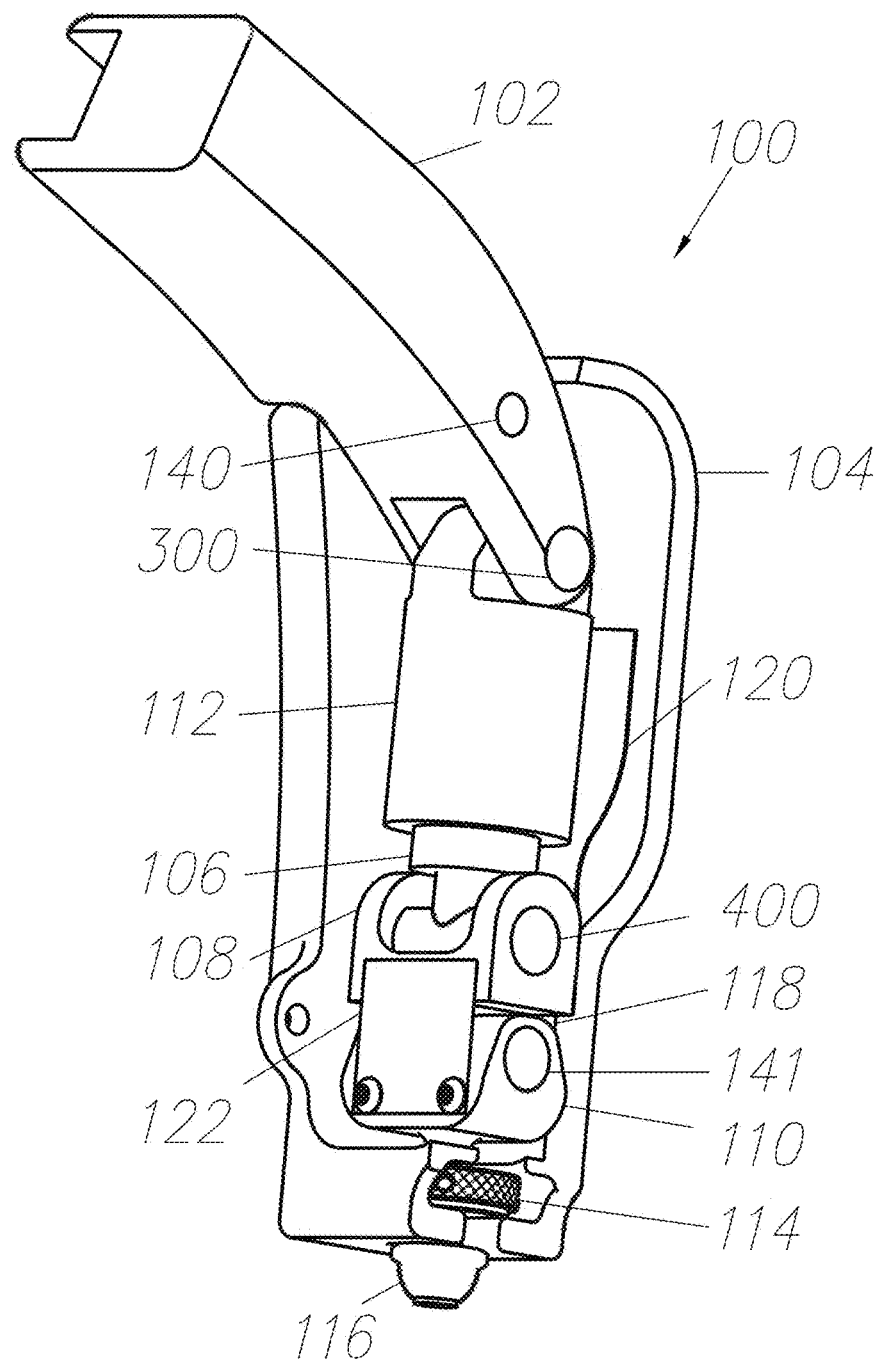
FIG. 12 depicts a cross-sectional view of the mechanical configuration as shown in FIG. 11.
Figure 13:
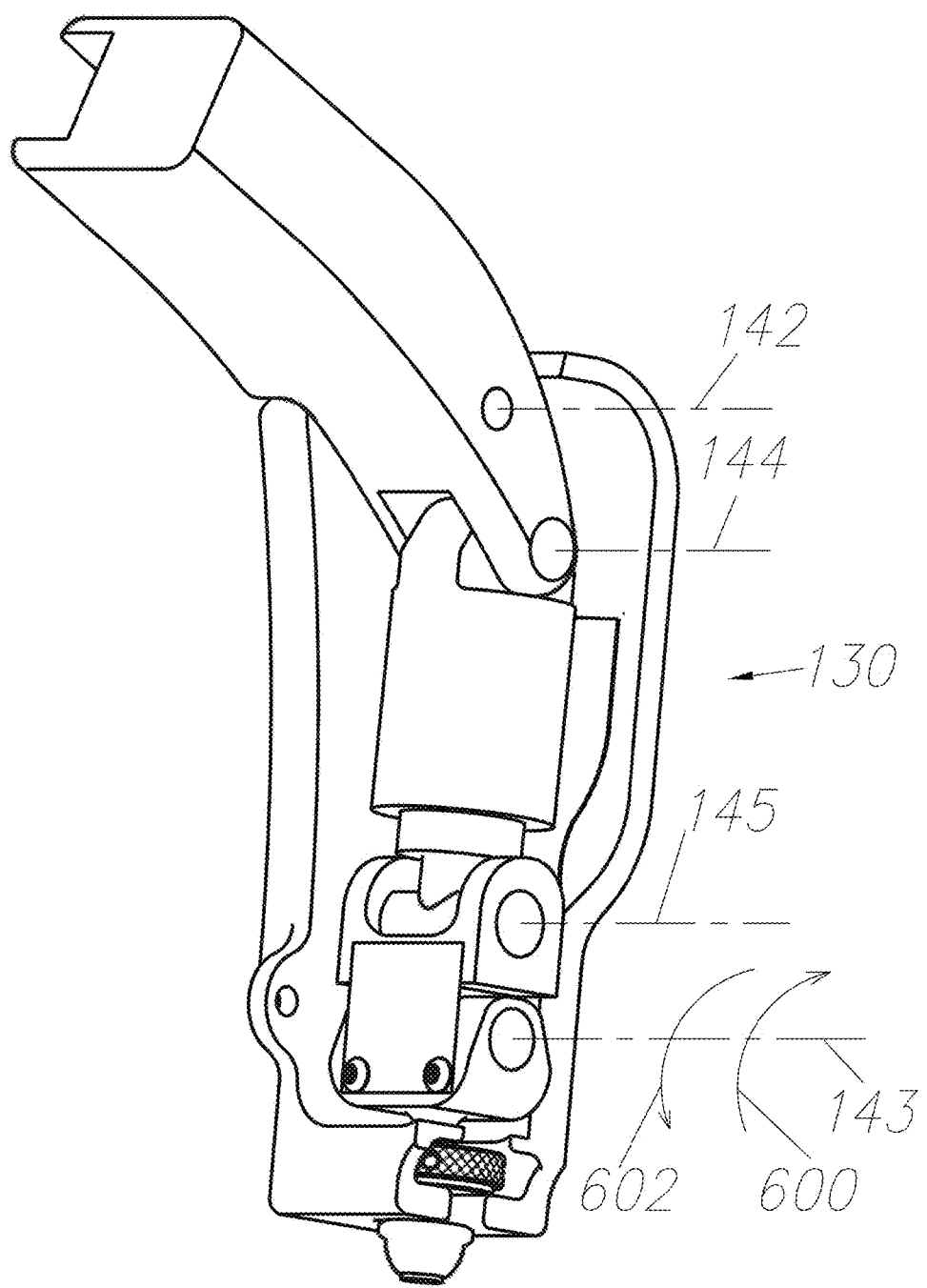
FIG. 13 depict a mechanical configuration as shown in FIG. 12 with an indication of the rotating axes of four bar linkage 130.

FIG. 11 shows an embodiment of artificial knee 100 which is designed based on the embodiments described above. FIG. 12 depicts a cross-sectional view of the mechanical configuration shown in FIG. 11. FIG. 13 is the same as FIG. 12, however it also shows all axes of rotations related to four bar linkage 130. In this embodiment, extension link 112 is rotatably coupled with thigh link 102, and linearly coupled with compression spring 106. Referring to FIG. 11, FIG. 12 and FIG. 13, artificial knee 100 comprises thigh link 102 configured to move in unison with the person's thigh. Artificial knee 100 further comprises shank link 104 which is configured to move in unison with the person's shank and rotatably coupled to thigh link 102. Thigh link 102 and shank link 104 rotate relative to each other about knee joint 140. Axis 142 represents the axis of knee joint 140 (rotation of thigh link 102 relative to shank link 104). Artificial knee 100 further comprises a compression spring 106 which is rotatably coupled to thigh link 102 at joint A 300. Axis 144 in FIG. 13 represents the rotation axis of joint A 300 (compression spring 106 relative thigh link 102). Compression spring 106 is rotatably coupled with fourth link 108 (follower link) from its second end 512 at Joint B 400. Axis 145 represents the rotational axis of joint B 400 (rotation of fourth link 108 relative compression spring 106). Fourth link 108 is rotatably coupled to shank link 104 at Joint C 141. Axis 143 represents the axis of joint C 141 (rotation of fourth link 108 relative to shank link 104).

Figure 15:
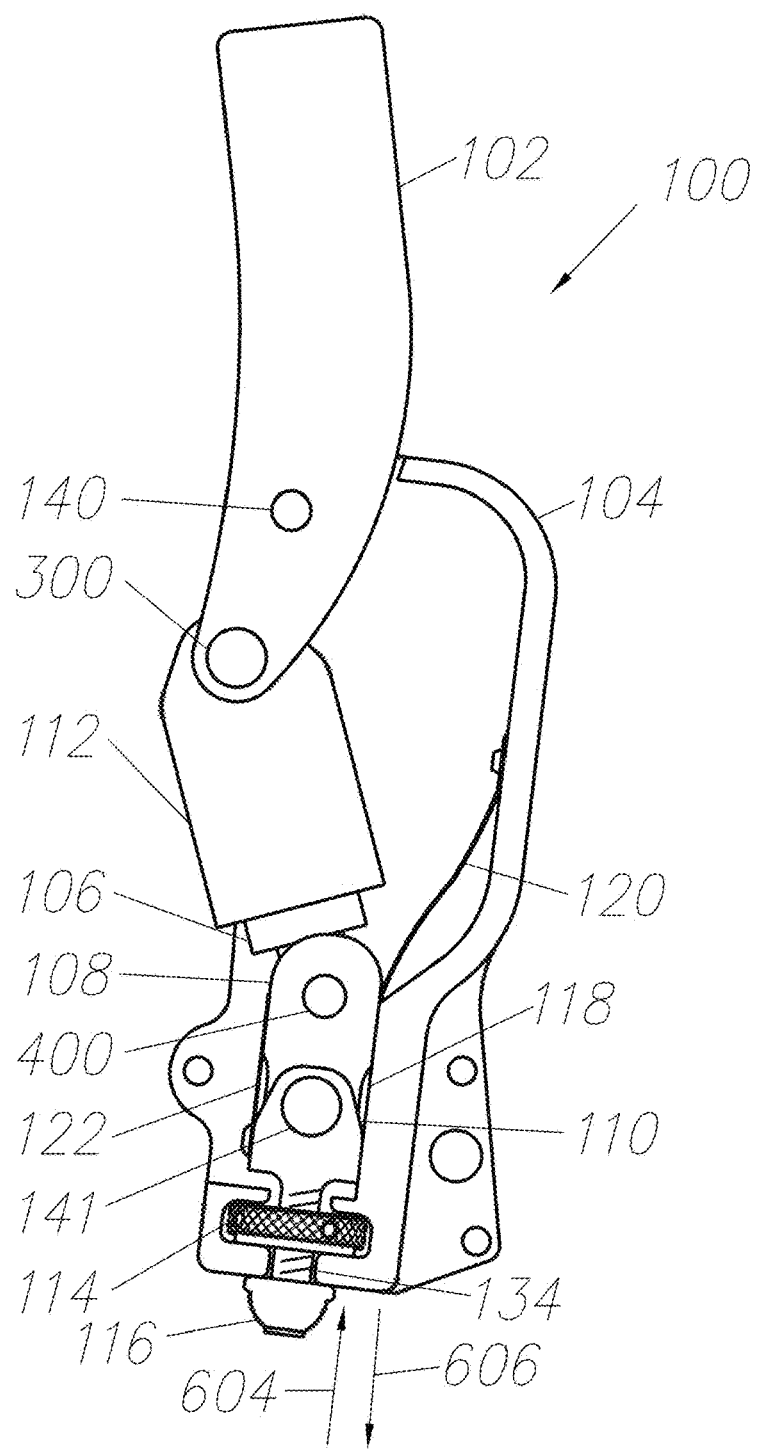
FIG. 15 shows how adjustment mechanism 132 can affect engagement angle 802.

FIG. 15 depicts a cross-sectional view of the mechanical configuration in FIG. 11. FIG. 15 is similar to FIG. 13, but focuses on first leaf springs 120 and second leaf spring 122. In this embodiment, artificial knee 100 further comprises first leaf spring 120. The first end of first leaf spring 120 is coupled to shank link 104, and the second end of first leaf spring 120 is configured to provide torque in direction 602 on follower link (fourth link 108). First leaf spring 120 causes fourth link 108 (follower link) to move along trajectory 164 as shown in FIG. 5B. Artificial knee 100 further comprises second leaf spring 122. The first end of second leaf spring 122 is coupled to shank link 104, and the second end of second leaf spring 122 is configured to provide torque in direction 600 on follower link (fourth link 108). Second leaf spring 122 causes fourth link 108 (follower link) to move along trajectory 162 as shown in FIG. 5A. In some embodiments, first leaf spring 120 and second leaf spring 122 can be combined into one single spring, or other type of torque generators such as magnet. Accordingly, first leaf spring 120 and second leaf spring 122 are configured to create torques causing follower link (fourth link 108) to move along trajectories 164 and 166.

Figure 14:
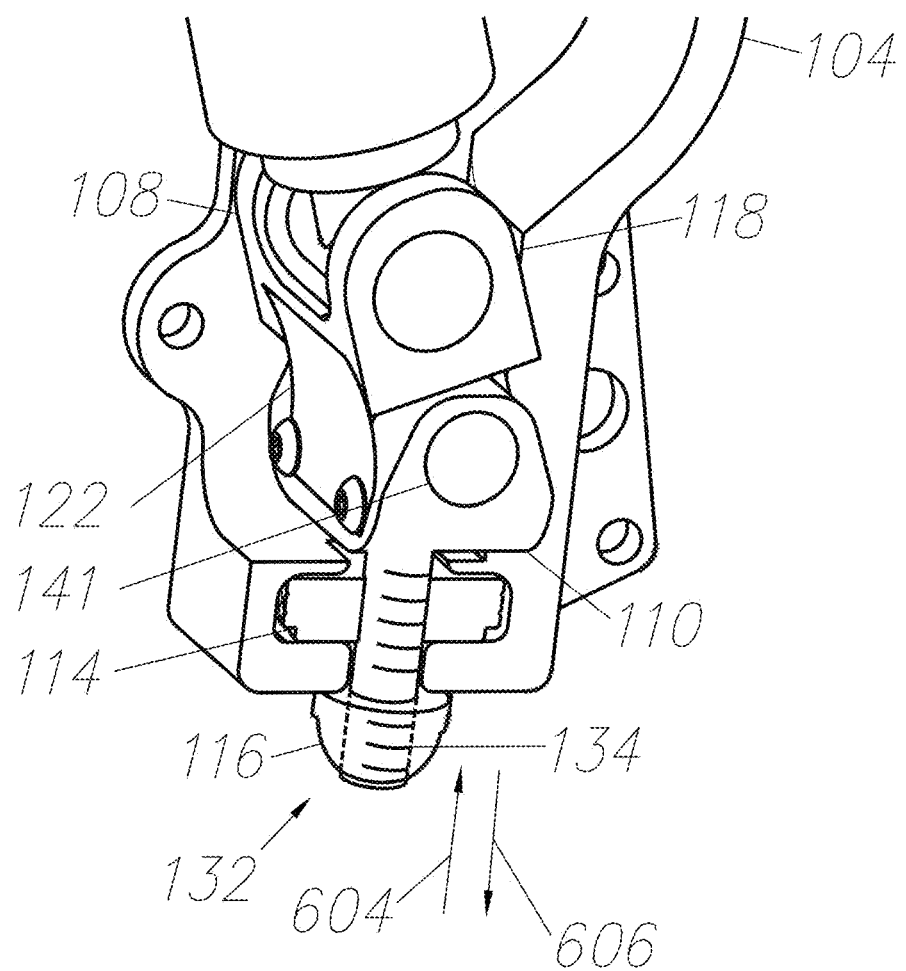
FIG. 14 depicts a cross-sectional view of the mechanical configuration shown in FIG. 11 focusing on adjustment mechanism 132.

As shown in FIG. 14, artificial knee 100 further comprises constraint 118. Constraint 118 is coupled to shank link 104. In some embodiments, constraint 118 is manufactured as a feature included in shank link 104. Constraint 118 blocks the motion of fourth link 108 when fourth link 108 moves along trajectory 162 shown in FIG. 5A.

Figure 16:
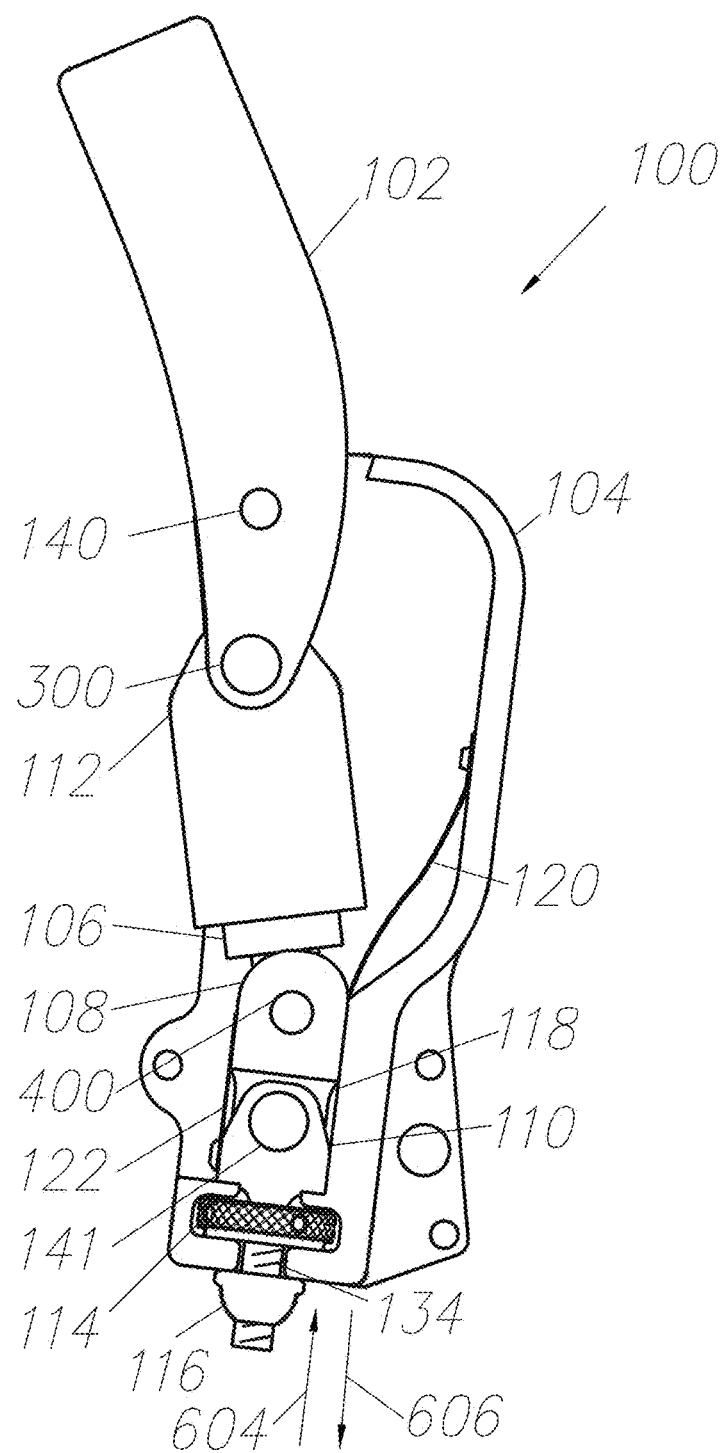
FIG. 16 shows how adjustment mechanism 132 can affect engagement angle 802 while adjuster 110 is moved in direction 606.

In some embodiments, as shown in FIG. 14, FIG. 15 and FIG. 16, artificial knee 100 further comprises an adjustment mechanism 132 to change the length between knee joint 140 and joint C 141. Accordingly, adjustment mechanism 132 is configured to allow the user to change the length of ground link (shank link 104) shown in FIG. 3. It will be discussed in greater detail below how this adjustment mechanism 132 allows various features of artificial knee 100. Adjustment mechanism 132 comprises adjuster 110 rotatably coupled to fourth link 108 from first end and slidably coupled to shank link 104 from another end. The external threads of adjuster 110 pass through a hole in shank link 104. Adjustment mechanism 132 further comprises thumb nut 114 and lock nut 116. By turning both thumb nut 114 and lock nut 116, adjuster 110 moves along direction 604 and 606 relative to shank link 104. This means the location of rotary joint C 141 with respect to knee joint 140 can be adjusted. The combination of thumb nut 114 and lock nut 116 secure adjuster 110 to shank link 104. It will be appreciated that various adjustment mechanisms may be implemented to change the length of ground link (shank link 104). FIG. 16 shows when adjuster 110 has moved along direction 606 in comparison with the configuration shown in FIG. 15. The engagement angle $\theta_{ENG}$ 802 in configuration of FIG. 16 is larger than the engagement angle $\theta_{ENG}$ 802 in configuration of FIG. 15.

Figure 17:
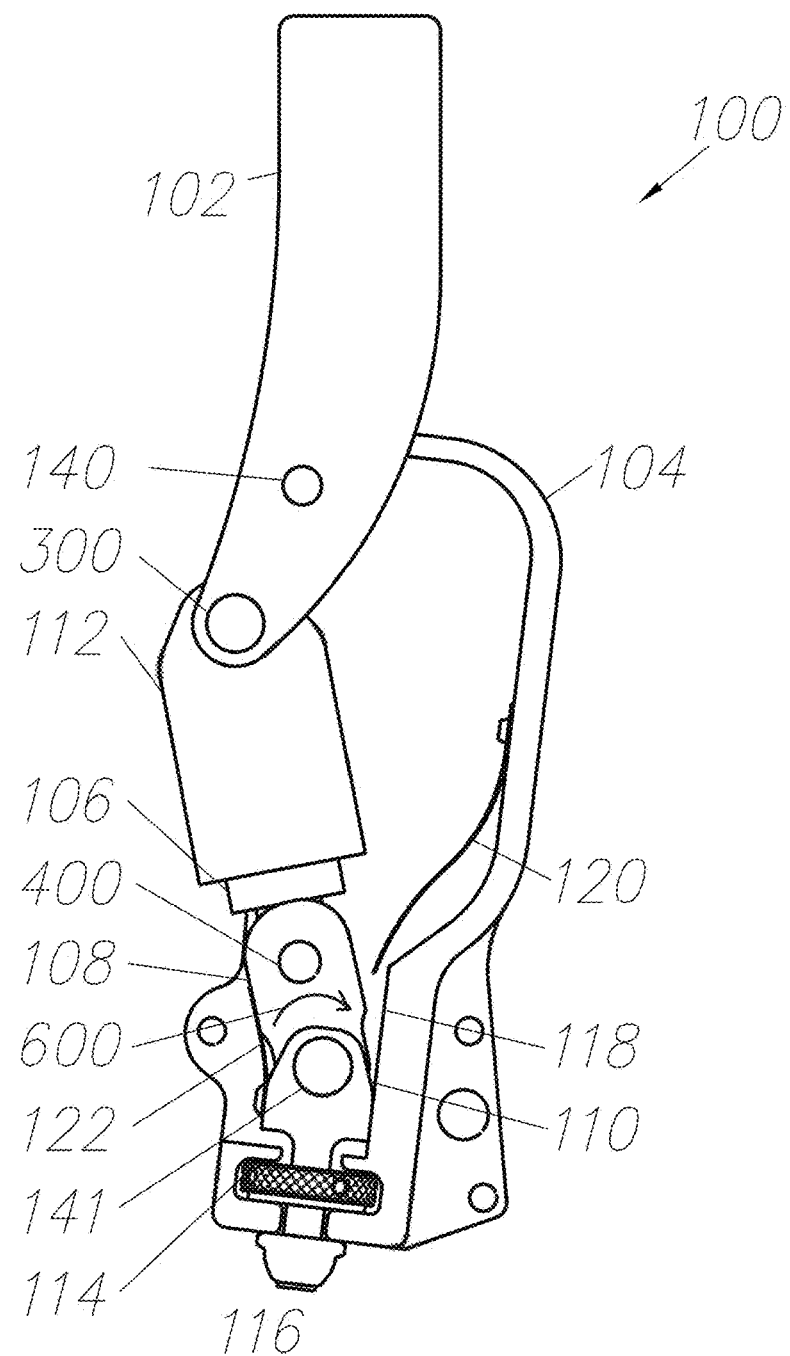
FIG. 17, FIG. 18, FIG. 19, FIG. 20, FIG. 21, and FIG. 22 depict how artificial knee 100 operates in a gait cycle in a cross-sectional view of the mechanical configuration in FIG. 11.

FIG. 17 through FIG. 22 depict artificial knee 100 at various knee angles throughout a gait cycle. FIG. 17 represents artificial knee depicted in FIG. 7A. FIG. 17 represents the configuration when knee angle $\theta_{KNEE}$ 700 is equal to start angle $\theta_{START}$ 800. In this configuration, coupler link (compression spring 106) aligns with follower link (fourth link 108). This configuration is schematically shown by FIG. 7A. Second leaf spring 122 pushes follower link (fourth link 108) with a torque along direction 600. Artificial knee 100 is at the border of the first free state and the second free state.

Figure 18:
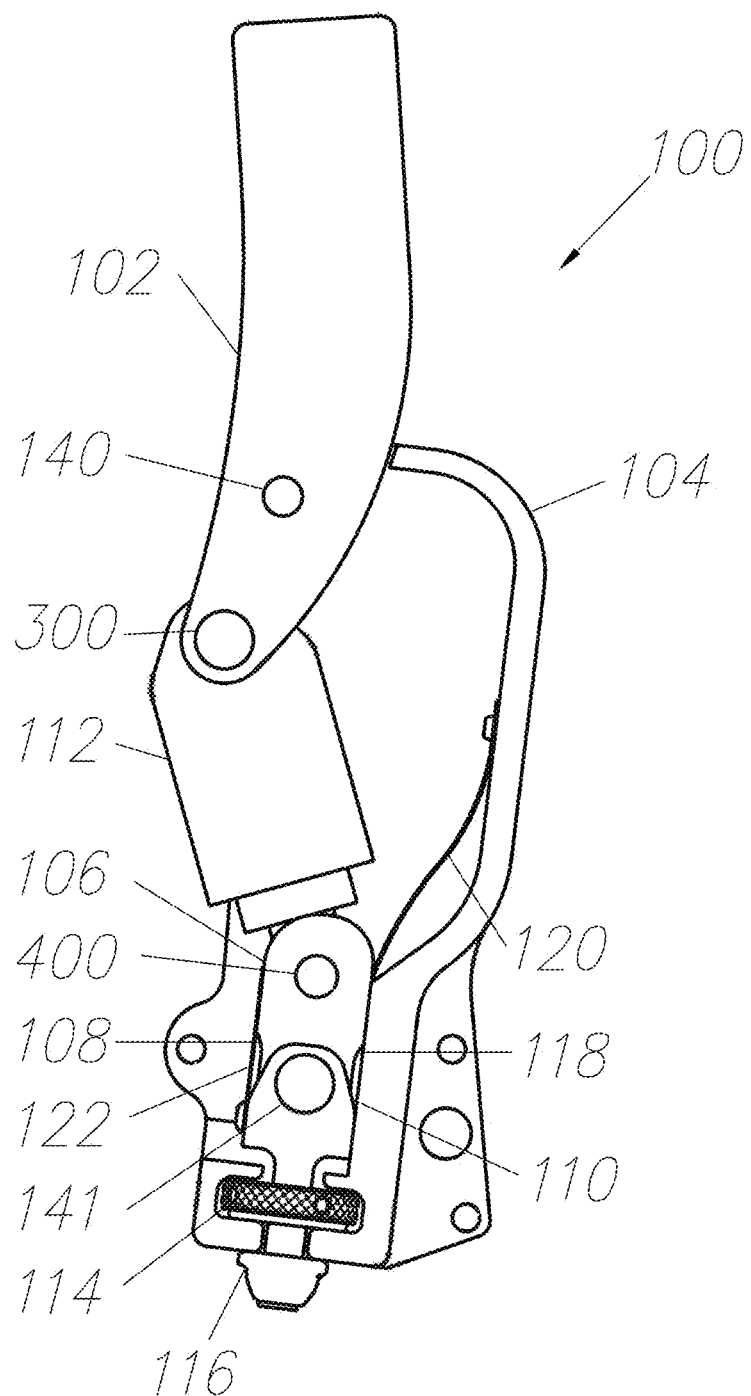
Figure 19:
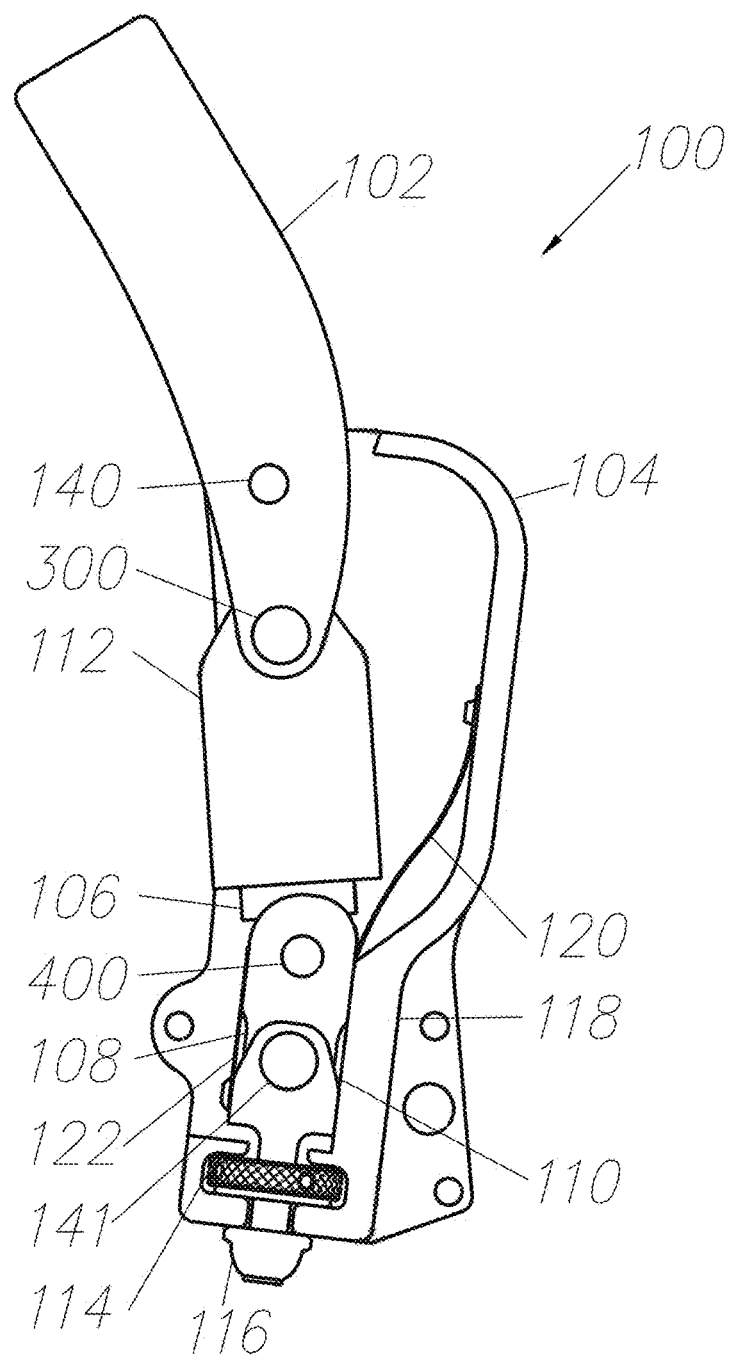
Figure 20:
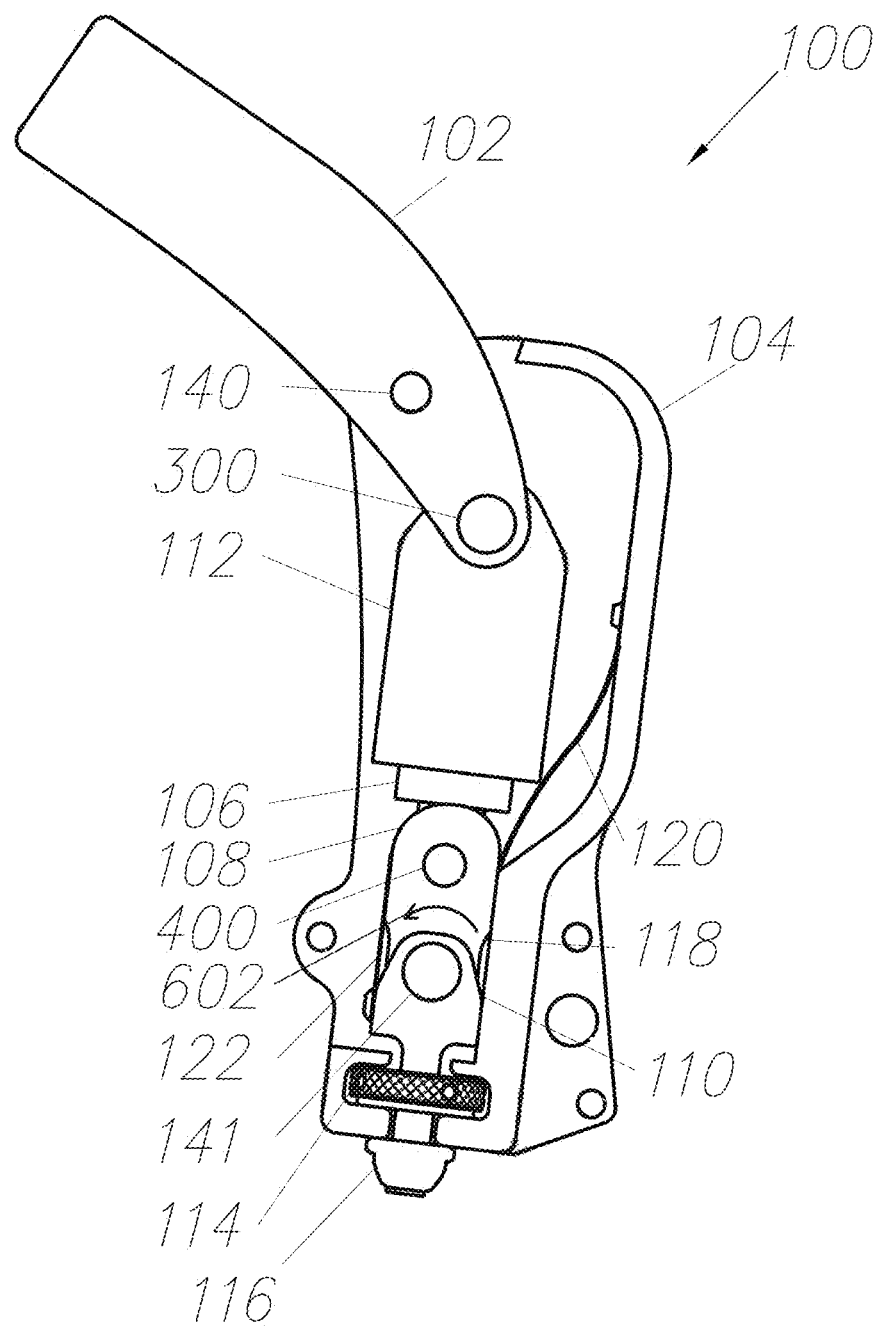

FIG. 18 depicts artificial knee 100 when fourth link 108 (follower link) is constrained (blocked) by constraint 118 and the compressive spring 106 is about to be compressed. Knee angle $\theta_{KNEE}$ 700 in FIG. 18 is equal to engagement angle $\theta_{ENG}$ 802. Artificial knee 100, at this instance, is at the border of the second free state and the extension support state. This configuration is schematically shown by FIG. 7B. After this instance, as knee angle $\theta_{KNEE}$ 700 increases, compressive spring 106 gets compressed (gets shorter) and provides extension torque about knee joint 140. FIG. 19 depicts artificial knee 100 when knee angle $\theta_{KNEE}$ 700 is equal to toggle angle $\theta_{TOG}$ 804. Fourth link 108 (follower link) is constrained by constraint 118 and compressive spring 106 aligns with knee joint 140. The torque from compressive spring 106 is zero at this instance and the compressive spring is at its maximum compression force. Artificial knee 100 at this instance is at the verge of the extension support state and the flexion support state. This is schematically shown in FIG. 7C. As knee angle $\theta_{KNEE}$ 700 increases, compressive spring 106 starts to provide flexion torque about knee joint 140 to encourage knee flexion. FIG. 20 depicts artificial knee 100 when knee angle $\theta_{KNEE}$ 700 is equal to release angle $\theta_{REL}$ 806. Fourth link 108, at this point is free to move away from constraint 118. Compressive spring 106, at this instant, completes generating compressive force and it returns to its original length. Artificial knee 100 at this instance is at the verge of the flexion support state and third free state. This is schematically shown in FIG. 7D. As knee angle increases after this instance, compressive spring 106 does not provide torque on knee joint 140.

Figure 21:
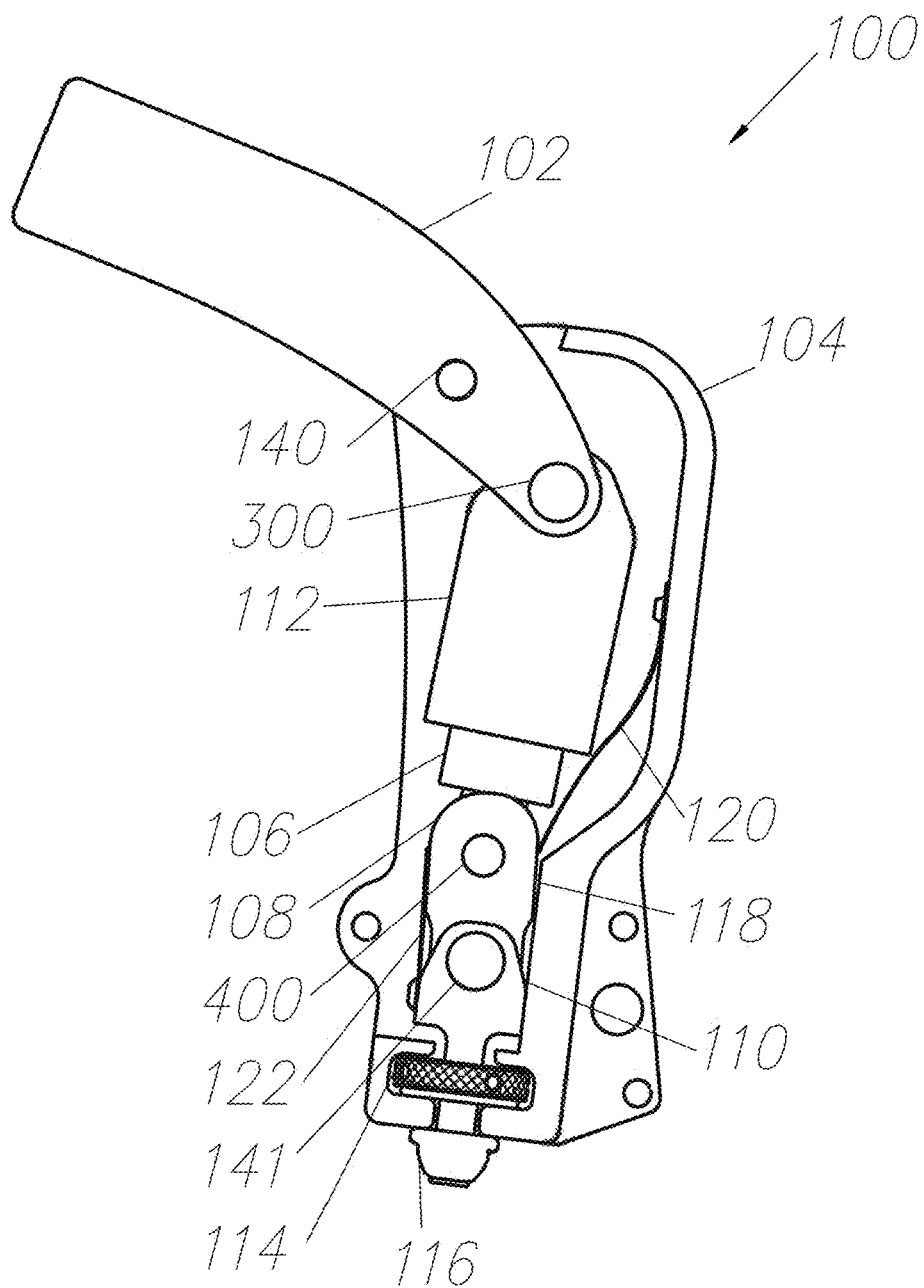
Figure 22:
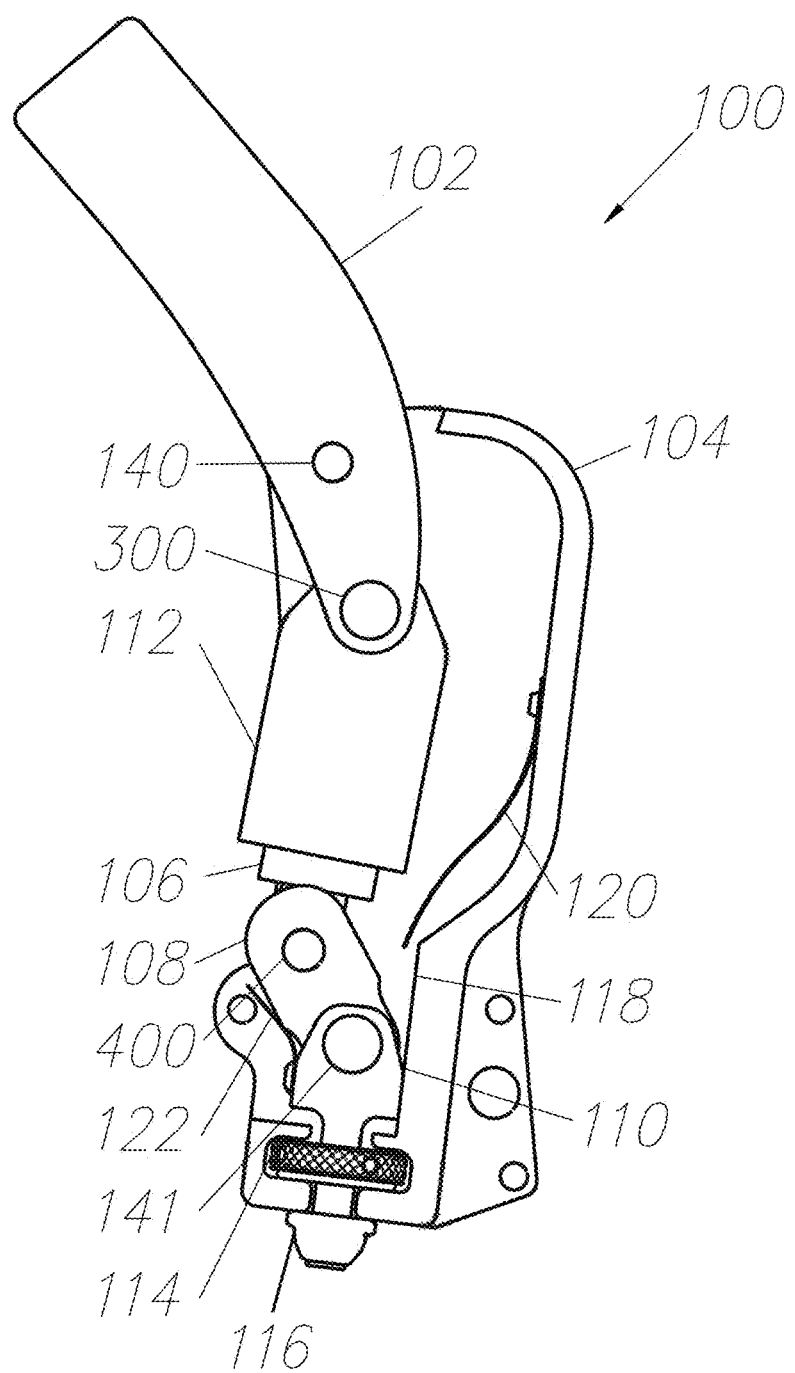
Figure 23:
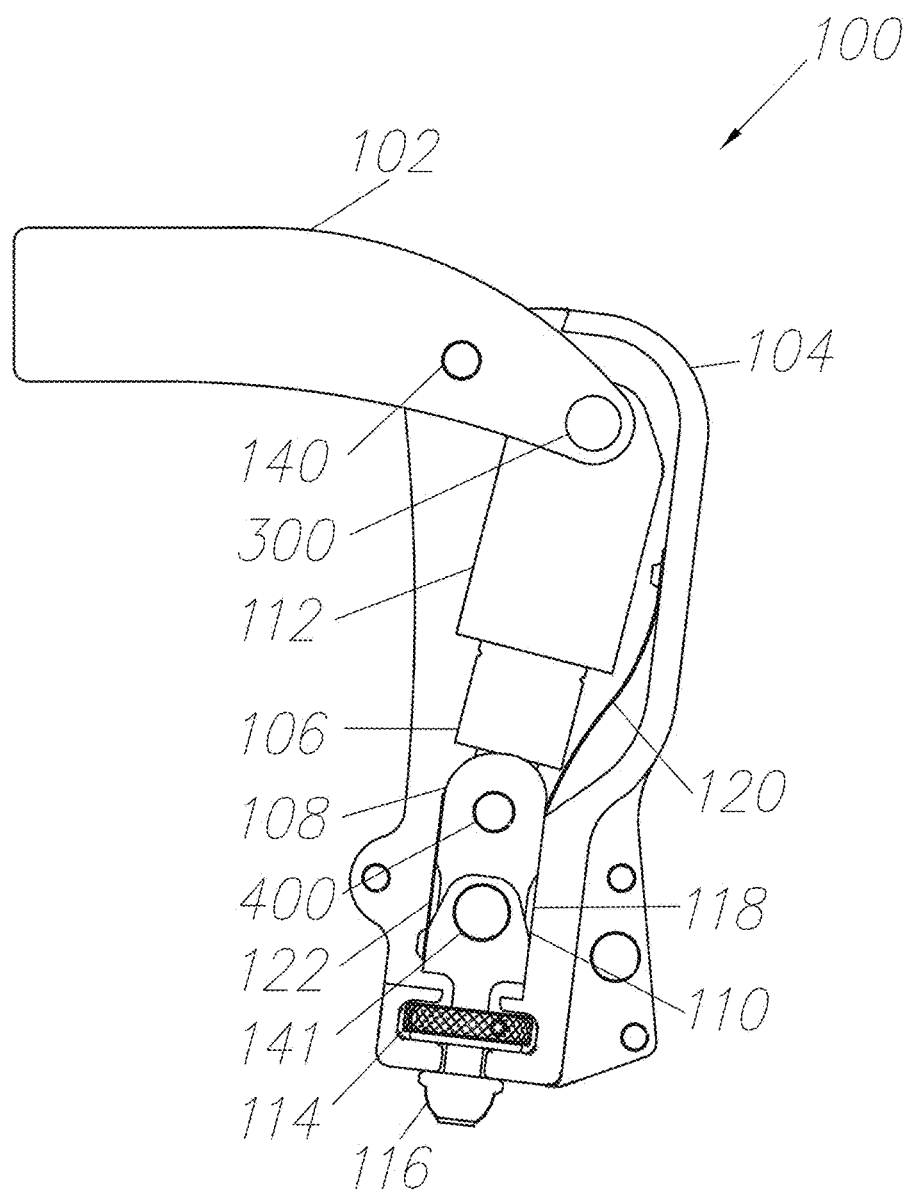
FIG. 23 depicts a cross-sectional view of the mechanical configuration of FIG. 11 when the knee angle $\theta_{KNEE}$ 700 is 90 degrees.

In this embodiment, end angle $\theta_{END}$ 808 is very close to release angle $\theta_{REL}$ 806. Therefore, the knee $\theta_{KNEE}$ 700 is at release angle $\theta_{REL}$ 806, which are virtually the same as end angle $\theta_{END}$ 808 in this embodiment as shown in FIG. 20, coupler link (compression spring 106) also aligns with follower link (fourth link 108), and first leaf spring 120 pushes the follower link (fourth link 108) to direction 602. The mechanism in this instance is also at the verge of the third free state and the first free state. This is schematically shown in FIG. 7E. FIG. 21 depicts artificial knee 100 when knee angle $\theta_{KNEE}$ 700 is larger than end angle $\theta_{END}$ 808. The extension of the extension link 112 allows knee angle $\theta_{KNEE}$ 700 to be able to go beyond end angle $\theta_{END}$ 808. Artificial knee 100 is in the first free state. As knee angle $\theta_{KNEE}$ 700 returns back to end angle $\theta_{END}$ 808, first leaf spring 120 pushes follower link (fourth link 108) in direction 602. FIG. 22 depicts artificial knee 100 when knee angle $\theta_{KNEE}$ 700 returns back to start angle $\theta_{START}$ 800 while artificial knee 100 is in the first free state. FIG. 23 depicts artificial knee 100 when knee angle $\theta_{KNEE}$ 700 is 90 degrees. Artificial knee 100 is in the first free state.

Figure 24:
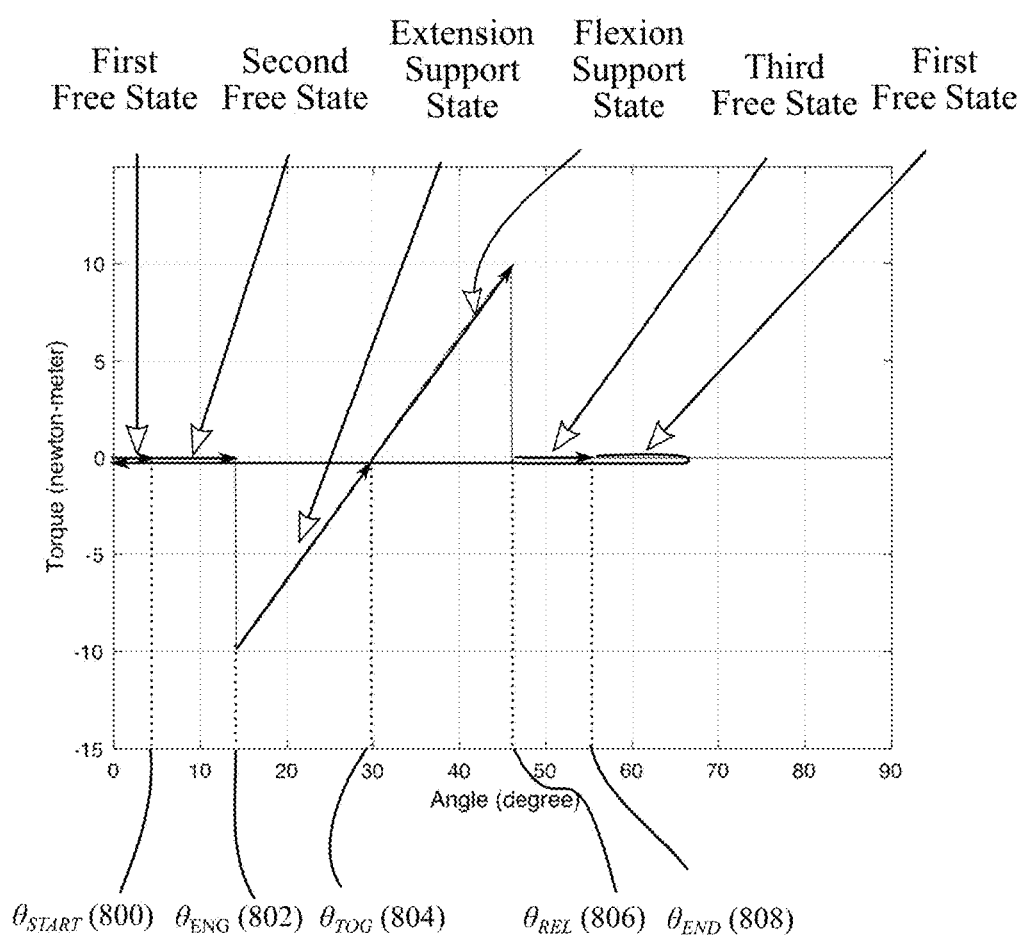
FIG. 24 depicts a torque profile of an embodiment of artificial knee 100.

FIG. 24 depicts a torque profile of an embodiment of artificial knee 100. In the first free state, the second free state, and the third free state, artificial knee 100 provides no torque. In extension support state, artificial knee 100 provides extension torque that attempts to decrease knee angle $\theta_{KNEE}$ 700. In flexion support state, artificial knee 100 provides flexion torque that attempts to increase knee angle $\theta_{KNEE}$ 700.

Figure 25A:
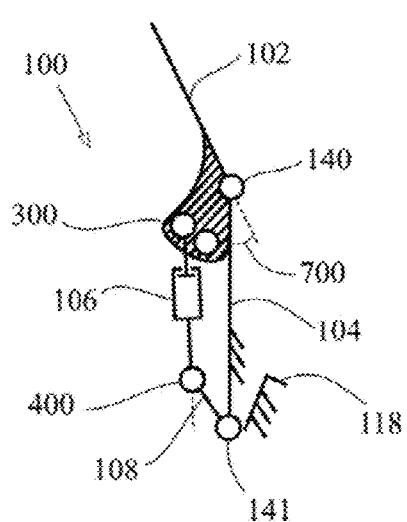
FIG. 25A and FIG. 25B depict an embodiment of artificial knee 100 where toggle angle 804 is adjustable.
Figure 25B:
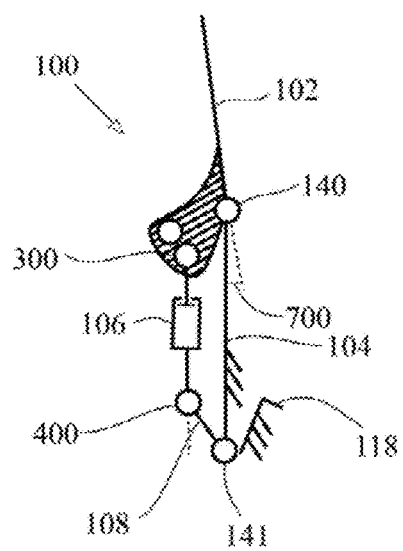

In some embodiments, toggle angle $\theta_{TOG}$ 804 is not adjustable. However, in other embodiments, toggle angle $\theta_{TOG}$ 804 is configured to be adjustable. The adjusting of the toggle angle is shown in FIG. 25A and FIG. 25B. Different locations of rotating point of the first end 510 of compressive spring 106 on the thigh link 102 provide options to switch toggle angle $\theta_{TOG}$ 804. It will be appreciated that various adjustment mechanisms may be implemented to change toggle angle $\theta_{TOG}$ 804.

FIG. 26 shows an embodiment of artificial knee 100 wearing by person 200 as an orthotics knee. FIG. 26 shows artificial knee 100 further connects to an ankle-foot orthotics 210. In some embodiments, such as the embodiment shown in FIG. 26, an ankle-foot orthosis 210 is configured to be coupled to a person's foot. In some embodiments, ankle-foot orthosis 210 is connectable to shank link 104. It will be appreciated that many forms of internal and external ankle-foot-orthoses may be implemented. In some embodiments, artificial knee 100 is coupled to person 200 through thigh brace 206 and shank brace 208. Although braces have been used to demonstrate the coupling of shank link 104 and thigh link 102 to the person's thigh 202 and person's shank 204 as shown in FIG. 26, it will be appreciated that many methods and devices can be implemented that would cause thigh link 102 and shank link 104 to move in unison with person's thigh 202 and person's shank 204; coupling through shank and thigh braces is just one method of causing the unison movement.

FIG. 27 shows an embodiment of artificial knee 100 wearing by person 200 as an exoskeleton knee. FIG. 27 shows artificial knee 100 further connects to exoskeleton 211 by connecting thigh link 102 to exoskeleton thigh 212, and shank link 104 to exoskeleton shank 214. In one embodiment, exoskeleton thigh 212 and exoskeleton shank 214 moves in unison with person's thigh 202 and person's shank 204 via thigh brace 206 and shank brace 208. In one embodiment, exoskeleton thigh 212 is rotatably coupled to exoskeleton trunk 216. In an alternative embodiment not shown, exoskeleton thigh 212 is coupled to exoskeleton trunk 216 by more than one rotary joints. It will be appreciated that exoskeleton components may be implemented in different forms. Similar to orthotics, there are many methods and devices in the exoskeleton context that would enable thigh link 102 and shank link 104 to move with person's thigh 202 and person's shank 204.

Figure 28:
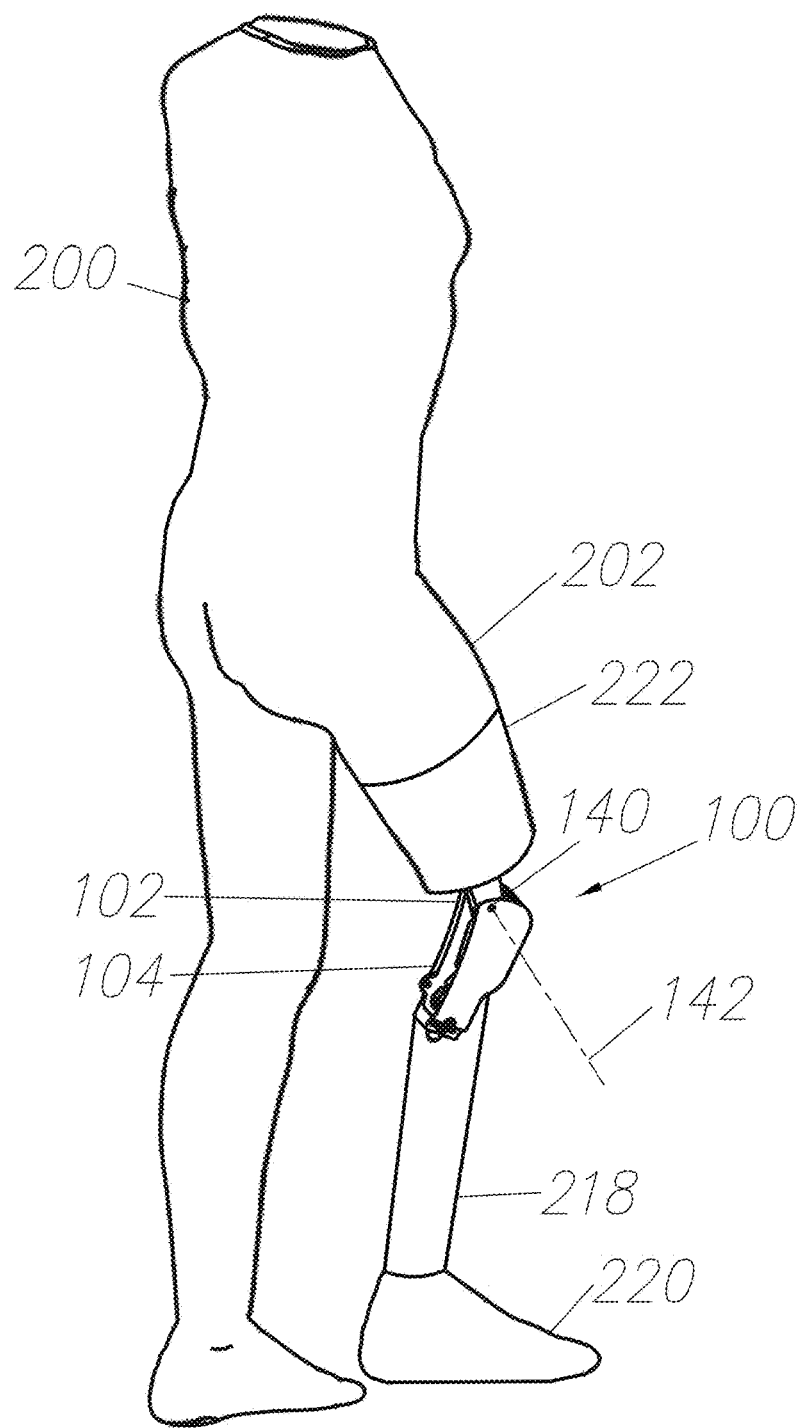
FIG. 28 shows an embodiment of artificial knee 100 worn by person 200 as a prosthetics knee.

FIG. 28 shows an embodiment of artificial knee 100 worn by person 200 as a prosthetics knee. In one embodiment as shown in FIG. 28, thigh link 102 connects with person's thigh 202 via socket 222. It will be appreciated that other methods and devices can be implemented that would cause thigh link 102 to move in unison with person's thigh 202. Shank link 104 connects to an artificial shank 218. In one embodiment as shown in FIG. 28, artificial shank 218 further connects to artificial foot 220. In an alternative embodiment not shown, artificial shank 218 comprises a leaf spring that is design to contact with the ground with compliancy. It will be appreciated that artificial shank 218 may be implemented in many different forms.

Figure 29A:
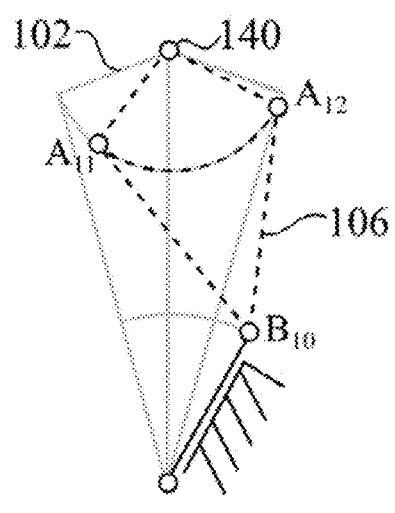
FIG. 29A and FIG. 29B depict how when adjuster 110 changes the distance between joint C 141 and knee joint 140, engagement angle 802 and release angle 806 can be adjusted.
Figure 29B:
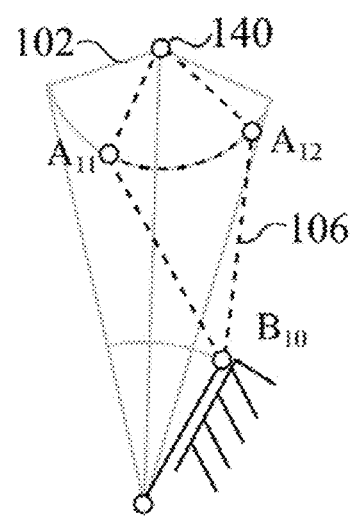

FIG. 29 depicts how when adjuster changes the distance between joint C 141 and knee joint 140, engagement angle 802 and release angle 806 can be adjusted as discussed in FIG. 15 and FIG. 16. FIG. 29B depicts the situation when adjuster 110 moved along direction 606 (shown in FIG. 14) compared to FIG. 29A. This means the length of ground link (shank link 104) is becoming larger from FIG. 29A to FIG. 29B. As shown in FIG. 29, the difference between release angle 806 (at which thigh link is at $A_{12}$) and engagement angle 802 (at which thigh link is at $A_{11}$) becomes smaller.

What is claimed is:

1. An artificial knee configured to be worn by a person, the artificial knee comprising:
    a thigh link configured to move in unison with a thigh of the person;
    a shank link configured to be rotatably coupled to the thigh link;
    a compression spring rotatably coupled to the thigh link at a first end;
    a follower link, wherein the compression spring is coupled to a second end of the shank link through the follower link such that the thigh link, the shank link, the follower link, and the compression spring form a four bar linkage comprising rotary joints; and
    a constraint configured to constrain the motion of the follower link relative to the shank link during a first range of motion and a second range of motion of the thigh link and the shank link relative to each other,
    wherein the compression spring is configured to provide an extension torque between the thigh link and the shank link during the first range of motion of the thigh link and the shank link relative to each other, and
    wherein the compression spring is configured to provide a flexion torque between the thigh link and the shank link during the second range of motion of the thigh link and the shank link relative to each other.

2. The artificial knee of claim 1, wherein the compression spring is configured to provide a force that passes through a coupling location of the thigh link relative to the shank link during a stance phase.

3. The artificial knee of claim 1, wherein the compression spring is configured to:
    resist the flexion of the thigh link relative to the shank link during the first range of motion of the thigh link and the shank link relative to each other, and encourage the flexion of the thigh link relative to the shank link during the second range of motion of the thigh link and the shank link relative to each other.

4. The artificial knee of claim 1, wherein the shank link is configured to move in unison with a shank of the person.

5. The artificial knee of claim 1, wherein during the motion of the thigh link and the shank link relative to each other, the compression spring is configured to provide a force that passes through the coupling location of the thigh link relative to the shank link at a time between the first and second ranges of motion of the thigh link and the shank link relative to each other.

6. The artificial knee of claim 1 further comprising:
a leaf spring configured to move the follower link from a singular point away from the constraint.

7. The artificial knee of claim 1, wherein the constraint is configured to block the motion of the follower link at a singular point, wherein the singular point is a point where the compression spring and the follower link are in line with each other.

8. An artificial knee configured to be worn by a person, the artificial knee comprising:
a thigh link configured to move in unison with a thigh of the person;
a shank link configured to move in unison with a shank of the person, and configured to be rotatably coupled to the thigh link;
a compression spring rotatably coupled to the thigh link at a first end of the compression spring, and rotatably coupled to the shank link at a second end of the compression spring,
a follower link rotatably coupled to the second end of the compression spring at a first end of the follower link, and rotatably coupled to the shank link at a second end of the follower link such that the thigh link, the shank link, the follower link and the compression spring form a four bar linkage; and
a constraint configured to constrain a motion of the follower link relative to the shank link during a range of motion of the thigh link relative to the shank link,
wherein during the range of motion where the constraint blocks the motion of the follower link, the compression spring is configured to provide a force such that the force passes through a coupling location of the thigh link and shank link relative to each other at a point during the motion of the thigh link relative to the shank link.

9. An artificial knee configured to be worn by a person, the artificial knee comprising:
a thigh link configured to move in unison with a thigh of a person;
a shank link configured to move in unison with a shank of the person, and configured to be rotatably coupled to the thigh link;
a compression spring rotatably coupled to the thigh link at a first end of the compression spring, and rotatably coupled to the shank link at a second end of the compression spring;
a follower link coupled to the compression spring and the shank link; and
a constraint configured to constrain a motion of the follower link relative to the shank link,
wherein when the follower link is moved from a singular point toward the constraint, the constraint blocks the follower link, and the compression spring provides an extension torque between the thigh link and the shank link during a first range of motion of the thigh link and the shank link relative to each other, and
wherein when the follower link is moved from the singular point away from the constraint, the constraint does not block the motion of the follower link, and flexion and extension of the thigh link relative to the shank link are unimpeded.

10. The artificial knee of claim 9 further comprising:
a leaf spring configured to move the follower link from the singular point away from the constraint.

11. An artificial knee configured to be worn by a person, the artificial knee comprising:
a thigh link configured to move in unison with a thigh of the person;
a shank link configured to move in unison with a shank of the person, and configured to be rotatably coupled to the thigh link;
a compression spring rotatably coupled to the thigh link at a first end of the compression spring, and rotatably coupled to the shank link at a second end of the compression spring;
a follower link rotatably coupled to the second end of the compression spring at a first end of the follower link, and rotatably coupled to the shank link at a second end of the follower link such that the thigh link, the shank link, the follower link and the compression spring form a four bar linkage;
a constraint configured to constrain a motion of the follower link relative to the shank link at a singular point, wherein the singular point is a point where the compression spring and the follower link are in line with each other,
wherein when the follower link is moved from the singular point toward the constraint, the constraint blocks the follower link and the compression spring provides a force such that the force passes through the knee joint at some point during a range of motion of the thigh link relative to the shank link.

* * * * *